(12) United States Patent
El-Say et al.

(10) Patent No.: US 11,298,321 B1
(45) Date of Patent: Apr. 12, 2022

(54) METHODS FOR TREATING METABOLIC DISORDER

(71) Applicant: King Abdulaziz University, Jeddah (SA)

(72) Inventors: Khalid M. El-Say, Jeddah (SA); Tarek A Ahmed, Jeddah (SA); Raed I. Felimban, Jeddah (SA); Hossam H. Tayeb, Jeddah (SA); Waleed Y Rizg, Jeddah (SA); Fuad H. AlNadwi, Jeddah (SA); Abdelsattar M. Omar, Jeddah (SA)

(73) Assignee: KING ABDULAZIZ UNIVERSITY, Jeddah (SA)

( * ) Notice: Subject to any disclaimer, the term of this patent is extended or adjusted under 35 U.S.C. 154(b) by 0 days.

(21) Appl. No.: 17/509,215

(22) Filed: Oct. 25, 2021

Related U.S. Application Data

(63) Continuation-in-part of application No. 17/372,654, filed on Jul. 12, 2021.

(51) Int. Cl.
*A61K 9/20* (2006.01)
*A61K 31/64* (2006.01)
*A61P 3/10* (2006.01)
*A61K 9/24* (2006.01)
*A61K 31/505* (2006.01)

(52) U.S. Cl.
CPC ............ *A61K 9/2095* (2013.01); *A61K 9/209* (2013.01); *A61K 9/2068* (2013.01); *A61K 31/505* (2013.01); *A61K 31/64* (2013.01); *A61P 3/10* (2018.01)

(58) Field of Classification Search
None
See application file for complete search history.

(56) References Cited

U.S. PATENT DOCUMENTS

| | | |
|---|---|---|
| 9,682,093 B2 | 6/2017 | Singh |
| 10,231,940 B2 | 3/2019 | Pather |
| 10,391,060 B2 | 8/2019 | Pilgaonkar |
| 10,952,974 B2 | 3/2021 | Sabliov |
| 10,973,767 B2 * | 4/2021 | Li ....................... A61K 9/2031 |
| 10,973,778 B2 | 4/2021 | Pather |
| 2020/0146994 A1 | 5/2020 | Albed Alhnan |

OTHER PUBLICATIONS

Khaled et al. "3D printing of tablets containing multiple drugs with defined release profiles". Oct. 30, 2015;494(2):643-650. doi: 10.1016/j.ijpharm.2015.07.067. Epub Jul. 30, 2015 (Year: 2015).*
Rejinold et al., "Curcumin-loaded biocompatible thermoresponsive polymeric nanoparticles for cancer drug delivery", Journal of Colloid and Interface Science 360: 39-51, 2011.
Rivera-Mancia et al., "Utility of curcumin for the treatment of diabetes mellitus: Evidence from preclinical and clinical studies", Journal of Nutrition & Intermediary Metabolism 14, 2018.
Enin et al., "Self-nanoemulsifying drug-delivery system for improved oral bioavailability of rosuvastatin using natural oil antihyperlipdemic", Drug Dev Ind Pharm, 41(7): 1047-1056, 2015.
Cheng et al., "3D printing of extended-release tablets of theophylline using hydroxypropyl methylcellulose (HPMC) hydrogels", International Journal of Pharmaceutics 591:119983, 2020.
Zhang et al., "Hydroxypropyl Methylcellulose-based Controlled Release Dosage by Melt Extrusion and 3D Printing: Structure and Drug Release Correlation", Carbohydr Polym. Dec. 1, 2017; 177: 49-57.
Giri et al., "Cellulose and its derivatives for application in 3D printing of pharmaceuticals" J. Pharm Investigation, published online: Sep. 4, 2020.
Zidan et al., "Development of mechanistic models to identify critical formulation and process variables of pastes for 3D printing of modified release tablets" Int. J. Pharmaceutics 555: 109-123, 2019, Abstract.
Polamaplly et al., "3D printing and characterization of Hydroxypropyl Methylcellulose and Methylcellulose for Biodegradable Support Structures" Procedia Manufacturing 34: 552-559, 2019.

* cited by examiner

*Primary Examiner* — Susan T Tran
(74) *Attorney, Agent, or Firm* — WC&F IP

(57) ABSTRACT

Provided are a self-nanoemulsifying 3D printer ink composition and a method of using such composition to manufacture a 3D-printed tablet having compartmentalized active pharmaceutical ingredients. In particular, the 3D-printed tablet composition includes glimepiride and/or rosuvastatin in a curcuma oil based self-nanoemulsifying drug delivery system (SNEDDS). The disclosure also provides a method of treating a metabolic disorder or disease by administering a therapeutically effective amount of the 3D-printed tablet to a subject in need thereof.

13 Claims, 20 Drawing Sheets

METHODS FOR TREATING METABOLIC DISORDER

CROSS REFERENCE TO RELATED APPLICATIONS

This application claims priority to and benefit of U.S. patent application Ser. No. 17/372,654 filed on Jul. 12, 2021, which is hereby incorporated by reference herein in its entirety.

FIELD OF THE INVENTION

The disclosure provides a self-nanoemulsifying 3D printer ink composition and a method of using such composition to manufacture a 3D-printed tablet having compartmentalized active pharmaceutical ingredients that are released in the body of a subject at a personalized drug-release rate. The disclosure also provides a method of using the 3D-printed tablet or polypill for treating a subject in need thereof. In particular, the tablet composition includes glimepiride and/or rosuvastatin in a curcuma oil based self-nanoemulsifying drug delivery system (SNEDDS).

BACKGROUND

Development of novel drug-loaded systems and implementing nanotechnology in drug delivery are useful in controlling and maintaining an adequate drug concentration in the target tissue. A plurality of examples implementing drug-loaded devices and/or nanomaterials as efficient drug delivery systems are known in the art. For example, the use of nanomaterials in personalized medicine is known to allow tailoring of medical devices or drug products to treat an individual patient or a group of related patients suffering a particular disease. The personalized medicine aims to ensure better health care with much lower cost by selecting the most appropriate and ideal therapy for individual patients (Vogenberg et al., 2010; Zilcha-Mano, 2020). To provide a tailored therapeutic treatment, a number of known diagnostic investigations on individual's genetic and molecular contents and/or other cellular analysis are usually employed into a routine clinical practice (Vogenberg et al., 2010). Personalized medicine is usually designed for patients that are not responding to traditional health system, which necessitates changes in the therapeutic practice manners and strategies of the health care professionals and medical device manufacturers.

Recent advances in personalized medicine generally depend on patient's genetic factors (i.e., human genomic information), which differ from one to another and thus result in more precise diagnosis of complex diseases (Lu et al., 2014). For instance, genomic sequencing can detect DNA mutations that may be implicated with specific diseases such as cystic fibrosis and cancer. A similar concept is applied to RNA sequencing which can correlate specific diseases to the change in the RNA molecules. In particular, RNA sequencing can assist in providing better understanding of the patients' health conditions since the changes in level of RNA are affected by environmental factors. RNA expression, translation and the level of body proteins have been linked to genetic differences between patients (Battle et al., 2014; Cenik et al., 2015; Wu et al., 2013). Scientists often conduct a genome-wide association study to investigate whether a particular mutation is associated to a certain disease. This is achieved by inspecting the sequence of the genome of many patients who are suffering from a specific disease and by correlating the result to specific mutations in the patients' genomic profiles. The collected results then may be used to diagnose the particular disease in future patients by comparing the genomic sequences of the patients to a reference of collected results to find the correlated mutation (Haines et al., 2005). Progresses in personalized medicine will find many applications in the diagnosis and treatment approaches especially for those who are suffering from genetic variations to provide a tailored drug prescription (Lesko, 2007).

The ability to fine-tune a formulation containing active pharmaceutical ingredient (API) and a therapeutic dose is aimed for minimizing therapeutics failures and the limitations of their side effects. The flexible control of drug formulations, doses and physicochemical properties can facilitate engineering of the dosage form based on the targeted patient's population and disease (Jamróz et al., 2018). For example, the drug dose may be optimized, especially for pediatric and geriatric patients whose physiological requirements may significantly vary from one another. During treatment of many chronic diseases, some drugs are administered individually, which might lead to errors in supplying these medications to geriatrics and in-patients, representing potential patient compliance issues. Therefore, an effective technology such as a 3D-printed and personalized pill that provides controllable drug release and is easy to produce may be useful. Such technology may significantly improve the quality of healthcare of chronic patients, and reduce resources, time, and financial burdens in manufacturing pharmaceuticals.

3D printing as a manufacturing platform holds a great promise in fabricating active pharmaceutical ingredients (API)s toward the personalization of medications. This is through a fine-tuning of the printing process parameters including the tablet's size and thickness of layers to control dosage form and/or the drug release by the use of 3D-printing technology in the development of personalized medicine which will produce an individualized drug delivery system in the pharmaceutical industry (Aguilar-de-Leyva et al., 2020). 3D-printing technology has become a powerful tool that has been employed in many pharmaceutical applications (Aimar et al., 2019). Therefore, formulation of a multi-drug via 3D-printing into a daily single dose tablet with appropriate release profiles will provide an attractive alternative method. The 3D-printing approach is a novel drug formulation manufacturing technique that can be used in the production of complex oral dosage delivery pharmaceuticals as tablets or pills using standard pharmaceutical materials in order to improve drug release profile of the commercially available dosage forms and the overall healthcare services of geriatric patients (Katstra et al., 2000).

Pharmaceutical manufacturing of currently marketed dosage forms, such as solid, semi-solid, liquid pharmaceuticals have been known and used for decades. However, any significant progress in terms of manufacturing flexibility and personalization has been slow. The traditional manufacturing processes of these dosage forms are applied to produce fixed drug doses based on mass production which cannot consider individual patient's condition and/or therapeutic plan requirements which may lead to a direct reflection on the quality of healthcare of chronic patients, and in reducing effort, time and financial obstacles in manufacturing of pharmaceuticals.

Patients need a tailored therapy to ensure better medical care. Selection of the appropriate therapy for a wide range of patients is based on an individual's genetic and/or molecular and cellular analysis. Of note, three-dimensional (3D) printing technology has been contemplated as a useful drug delivery manufacturing system in that a 3D structure can be manufactured by fusing or depositing of different materials by applying the strategy of layer-by-layer additive manufacturing. Medical 3D printing can support pharmaceutical companies to produce more specific drug delivery systems, enabling a rapid production of medical devices, and changing the way that doctors and surgeons plan procedures. Patient-specific 3D-printed medications are becoming increasingly beneficial in personalized treatments, especially for the practice of precision medicine.

However, despite the advantageous features of the current 3D printed medications, there are several factors that may be of concern to the effectiveness of the 3D printed drug delivery system. For example, many active pharmaceutical ingredients (APIs) do not reach the commercialization step due to their limited oral bioavailability. Another important current problem in the pharmaceutical industry for drugs of limited bioavailability is mainly attributed to their inadequate aqueous solubility and dissolution rate. Moreover, a high percent of the administered drug is lost during the absorption process due to the first-pass metabolism phenomenon.

Thus, there is a need for a composition and a method for providing an improved 3D printed drug delivering tablet with increased aqueous solubility and dissolution rate for ease of bioavailability.

SUMMARY OF THE INVENTION

An object of the invention is to provide a self-nanoemulsifying 3D printer ink composition and a method of using such composition to manufacture a 3D-printed tablet having compartmentalized active pharmaceutical ingredients with customizable drug release rates. The disclosure also provides a method of administering the 3D-printed tablet to a subject for treating a metabolic disorder. One of the main advantageous features of the present disclosure includes a significantly improved bioavailability of the multi-compartmentalized tablet to provide personalized pharmaceutical treatment to a patient in need thereof. In particular, the 3D printed tablet composition of the present disclosure includes glimepiride and/or rosuvastatin in a curcuma oil based self-nanoemulsifying drug delivery system (SNEDDS) for enhanced bioavailability having doses of glimepiride and/or rosuvastatin designed to be responsive to the individual patient's needs. The compartmentalized tablet allows for personalization of not only the dose of different biologically active agents in the same dosage unit, but also customization of the release behavior for each incorporated drug.

One aspect of the disclosure provides a self-nanoemulsifying drug delivery system (SNEDDS) 3D printer ink composition that comprises glimepiride (GLMP), rosuvastatin (RSV) or pharmaceutically acceptable salts thereof, 10-20 wt. % of curcuma oil, 5-20 wt. % of one or more surfactants, 70-80 wt. % of one or more co-surfactants, and 2-10% w/v of hydroxypropyl methylcellulose (HPMC) as a gelling agent. In some embodiments, the one or more surfactants may also be selected from the group of polyoxyethylene sorbitan monooleate, sorbitan esters, nonionic polyoxyethylene, caprylocaproyl polyoxyl-8 glycerides, and polyoxyethylated triglycerides castor oil. The composition may include one or more co-surfactants that are selected from the group of polyethylene glycol (PEG), propylene glycol monolaurate, diethylene glycol, PEG 200, PEG 400, ethanol, isopropanol, butanol and pentanol. In preferred embodiments, the composition further comprises one or more soluble fillers, one or more insoluble fillers and one or more disintegrants. In some embodiments, the one or more soluble fillers are selected from the group of polyvinyl pyrrolidone (PVP) K90, lactose and cellulose ether (e.g., Methocel®). In some embodiments, the one or more insoluble fillers may be microcrystalline cellulose (e.g., Avicel®). In some embodiments, the composition comprises croscarmellose sodium (e.g., Ac-Di-Sol®) as a disintegrant. In some embodiments, the composition comprises glimepiride (GLMP) and rosuvastatin (RSV) at a weight ratio of about 3:1-1:3.

Another aspect of the present disclosure provides a method of preparing a self-nanoemulsifying drug delivery system (SNEDDS) 3D-printed tablet having glimepiride (GLMP), rosuvastatin (RSV) and/or pharmaceutically acceptable salts thereof, comprising the steps of: mixing curcuma oil, one or more surfactants and one or more co-surfactants, and water to form a first homogenous nanoemulsion; incorporating glimepiride (GLMP) and/or pharmaceutically acceptable salts thereof into the first homogenous nanoemulsion; mixing curcuma oil, one or more surfactants, one or more co-surfactants, and water to form a second homogenous nanoemulsion; incorporating rosuvastatin (RSC) and/or pharmaceutically acceptable salts thereof into the second homogenous nanoemulsion; mixing a gelling agent into the first and second homogenous nanoemulsions; blending one or more pharmaceutical excipients into the first and second homogenous nanoemulsions to form a first and second gel paste; loading the first and second gel paste into a 3D printer; and printing a multi-compartmentalized tablet.

In some embodiments, the one or more pharmaceutical excipients are 15-25 wt. % of microcrystalline cellulose, 8-12 wt. % of polyvinylpyrrolidone, 8-12 wt. % of lactose, 3-8 wt. % of cellulose ethers and 3-8 wt. % of croscarmellose sodium. In some embodiments, the nanoemulsion may also include one or more surfactants selected from the group of polyoxyethylene sorbitan monooleate, sorbitan esters, nonionic polyoxyethylene, caprylocaproyl polyoxyl-8 glycerides, and polyoxyethylated triglycerides castor oil. The homogenous nanoemulsion may include one or more co-surfactants that are selected from the group of polyethylene glycol (PEG), propylene glycol monolaurate, diethylene glycol, PEG 200, PEG 400, ethanol, isopropanol, butanol and pentanol. In some embodiments, the gelling agent is selected from polyacrylic acid (e.g., Carbopol®), xanthan gum, gelatin and HPMC. The printed multi-compartmentalized tablet may have two compartments for incorporating glimepiride (GLMP) and/or rosuvastatin (RSV) into each compartment to be released with varying drug releasing rates in the body of a subject in need thereof. The 3D printed tablet may comprise additional pharmaceutically active agents encapsulated in the same or different compartments for varying drug-release rates to treat multiple related pathogenic conditions such as cardiovascular, cancer, autoimmune disease and/or diabetes.

Embodiments of the present disclosure also include a method of treating a metabolic disorder or disease in a subject in need thereof by administering the 3D printed tablet to the subject in an amount sufficient to treat the metabolic disorder or disease, wherein the 3D printed tablet comprises glimepiride (GLMP), rosuvastatin (RSV) and/or pharmaceutically acceptable salts thereof; and 10-20 wt. % of curcuma oil in a self-nanoemulsifying drug delivery system (SNEDDS), wherein the 3D-printed tablet is a multi-compartmentalized tablet having at least one layer of GLMP and at least one layer of RSV in separate compartments, and wherein each compartment is configured to release GLMP or RSV at a different rate.

Additional features and advantages of the present invention will be set forth in the description of disclosure that follows, and in part will be apparent from the description of may be learned by practice of the disclosure. The disclosure will be realized and attained by the compositions and methods particularly pointed out in the written description and claims hereof.

DETAILED DESCRIPTION

Figure 1A:
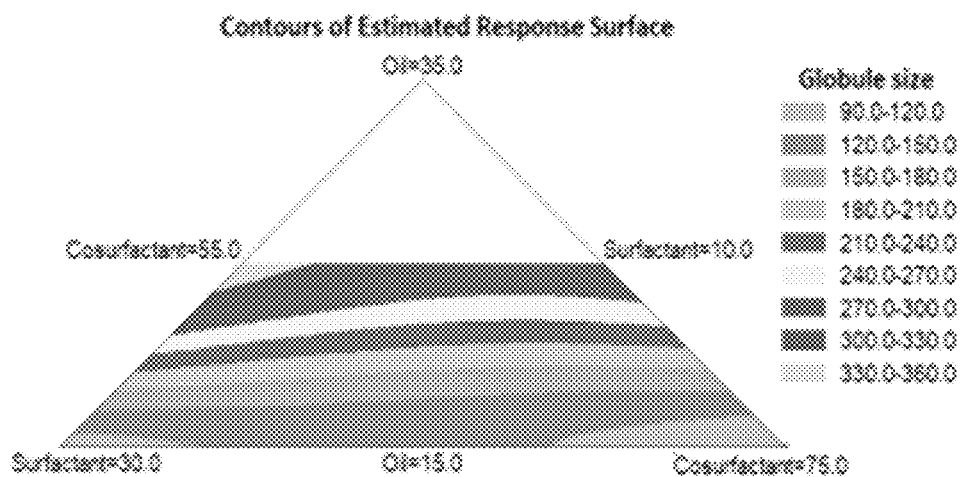
FIGS. 1A-B show (A) contour and (B) estimated response surface plots which demonstrate the effect of oil, surfactant and co-surfactant on the globule size.

The preferred embodiments of the present disclosure are directed toward a 3D printed ink composition for an orally administered tablet. The present disclosure provides a method of using the 3D-printed tablet for treating a subject with a metabolic disorder or disease. The present disclosure also provides a method of using the composition for manufacturing a 3D printed tablet containing at least one pharmaceutically active material to be released upon administration to a subject in need thereof. The composition is particularly formulated with an aid of a natural oil isolated from a plant to provide superior bioavailability.

One aspect of the disclosure provides a self-nanoemulsifying drug delivery system (SNEDDS) 3D printer ink composition that comprises glimepiride (GLMP) and/or rosuvastatin (RSV). The composition further comprises 5-30 wt. %, preferably 8-25 wt. %, more preferably 10-20 wt. % of curcuma oil. In some embodiments, the composition comprises 50-95 wt. %, preferably 60-90 wt. %, more preferably 70-80 wt. % of one or more co-surfactants and 2-40 wt. %, preferably 4-30 wt. % more preferably 5-20 wt. % of one or more surfactants. In preferred embodiments, 2-10% w/v of hydroxypropyl methylcellulose (HPMC), polyacrylic acid, xanthan gum or gelatin is incorporated as a gelling agent. The composition comprises active pharmaceutical ingredients, for example, any types of drugs or therapeutic agents that are used for treating a subject in need thereof. In preferred embodiments, glimepiride (GLMP) and rosuvastatin (RSV) are incorporated in the composition at a 3:1-1:3 weight ratio as to be used for a customizable diabetes and/or cardiovascular diseases treatment. The concentration of GLMP and/or RSV in the 3D printed tablet composition may vary depending on the individual patient's needs as well as the amount and frequency of each dosage. For example, a 3D printed tablet with a 50 mg dry weight may comprise 1-45 mg, preferably 5-42 mg, more preferably 4-40 mg of GLMP and/or RVS. In some embodiments, glimepiride (GLMP), rosuvastatin (RSV) and/or pharmaceutically acceptable salts thereof has a concentration to provide a sufficient pharmaceutical response in an individual subject.

In some embodiments, the one or more surfactants may also be selected from the group of polyoxyethylene sorbitan monooleate, sorbitan esters, nonionic polyoxyethylene, caprylocaproyl Polyoxyl-8 glycerides, and polyoxyethylated triglycerides castor oil. In some embodiments, the composition may include one or more co-surfactants that are selected from the group of polyethylene glycol (PEG), propylene glycol monolaurate, diethylene glycol, PEG 200, PEG 400, ethanol, isopropanol, butanol and pentanol. In preferred embodiments, the self-nanoemulsifying drug delivery system composition further comprises one or more soluble fillers, one or more insoluble fillers and one or more disintegrants. In some embodiments, the soluble filler is selected from the group of polyvinyl pyrrolidone (PVP) K90, lactose and cellulose ether (e.g., Methocel®). In some embodiments, the insoluble filler is microcrystalline cellulose (MCC, e.g., Avicel®). In some embodiments, the composition comprises croscarmellose sodium (e.g., Ac-Di-Sol®) as a disintegrant. Other suitable disintegrants that may be employed include, but not limited to, crospovidone, calcium silicate, sodium starch glycolate, starch and the like or combinations thereof. Suitable superdisintegrants that may be employed include, but are not limited to, natural, modified or pregelatinized starch, crospovidone, croscarmellose sodium, sodium starch glycolate, low-substituted hydroxypropyl cellulose and the like or combinations thereof.

As used herein, the term "self-nanoemulsifying drug delivery system (SNEDDS)" means anhydrous homogenous liquid mixtures consisting of oil, surfactant, drug and co-emulsifier or solubilizer which spontaneously form oil-in-water nanoemulsion of approximately 20-200 nm (or less than 20 nm) in size upon dilution with water under gentle agitation. The composition of the SNEDDS may be optimized with the help of phase diagrams and to improve bioavailability of hydrophobic drugs by several routes of administration. In addition, the SNEDDS formulations may be filled in soft and hard gelatin capsules. In some embodiments, SNEDDS comprises PEG 400 and tween. In another embodiments, SNEDDS further comprises of linoleic acid or the like functional component (e.g. olive oil, linoleic acid, oleic acid, etc.). The SNEDDS described herein may be used in any of a variety of therapeutic applications, e.g. 1) they may be administered through numerous routes, examples of routes include but are not limited to intranasal, oral-route forms such as gel capsules granules or suspensions or solutions, sublingual and buccal administration forms, aerosols, implants, subcutaneous, transdermal, topical, intraperitoneal, intramuscular, intravenous, subdermal, transdermal, intrathecal, intraduodenal, and rectal administration forms, 2) they may be used as a therapeutic treatment option for a various disorders including diabetes, cardiovascular diseases, CNS-related disorders such as acute stroke, cerebral vascular ischemia, cerebral dysfunction and Alzheimer's disease and/or used as a supplement for improving symptoms of dementia, energy metabolism, weight loss, and anti-aging.

To enhance bioavailability of the SNEDDS composition, curcuma oil (also known as "turmeric" oil) of either in an extracted or purified form is included in the SNEDDS 3D printer ink composition. In some embodiments, the curcuma oil is an extract from the *Curcuma* or *Curcuma* L genus, in which the list of *Curcuma* genus is provided in U.S. Pat. No. 10,231,940 to Pather, herein incorporated by reference. In other embodiments, other types of pharmaceutically acceptable oil or any combination of oils may be used in the composition. Some exemplary types of oils include an animal oil, a fish oil, a vegetable oil, a mineral oil, olive oil, sunflower oil, sesame oil, almond oil, corn oil, orange oil, lime oil, black petter oil, nutmeg oil, basil oil, rosemary oil, clove oil, grapefruit oil, fennel oil, coriander oil, bergamot oil, cinnamon oil lemon oil, peppermint oil, garlic oil, thyme oil, marjoram oil, lemongrass oil, ginger oil, cardamom oil, liquid paraffin, cotton seed oil, peanut oil, nut oil, soy oil, rapeseed oil, vitamin E oil, Vitamin E TPGS oil, tallow-derived oil, fish oil, silicone oil, castor oil, squalene oil or any combinations thereof.

In some embodiments, co-surfactants were selected from the group of sorbitan esters (e.g., Spans®), nonionic polyoxyethylene (e.g., Brij®), caprylocaproyl Polyoxyl-8 glycerides (e.g., Labrasol®), and polyoxyethylated triglycerides castor oil (e.g., Cremophor EL®). Other co-surfactants may be used, for example, nonionic copolymers comprised of a central hydrophobic polymer (polyoxypropylene polypropylene oxide) with a hydrophilic polymer (polyoxyethylene polyethylene oxide) on each side, polyethylene ethers, sorbitan esters, polyoxyethylene sorbitan esters, polyoxyethylene fatty acid esters, polyoxyl castor oils, polyoxyl hydrogenated castor oils, macrogol cetostearyl ethers, macrogol lauryl ethers, macrogol oleyl ethers, macrogol stearates, polyoxamers, and mixtures thereof. Non-limiting examples of nonionic surfactants suitable for the present disclosure may include: Pluronic® surfactants which are nonionic copolymers composed of a central hydrophobic polymer (polyoxypropylene polypropylene oxide) with a hydrophilic polymer (polyoxyethylene polyethylene oxide) on each side, with exemplary products including Pluronic® L-31, L-35, L-61, L-81, L-64, L-121, L-123, F-68, and F-108. Brij® are nonionic surfactants comprising polyethylene ethers and exemplary commercially available products include Brij 30, 35, 52, 56, 58, 72, 76, 78, 92V, 93, 96V, 97, 98 and 700. Span® are nonionic surfactants comprising sorbitan esters and exemplary products include Span 20, 40, 60, 65, 80 and 85. Tween® (polysorbates) are nonionic surfactants comprising polyoxyethylene sorbitan esters. Various commercially available Tween® products may be used in the composition, exemplary products including Tween 20, 40, 60, 65, 80 and 85. Myrj® are nonionic surfactants comprising polyoxyethylene fatty acid esters. Various commercially available Myrj® products may be used, exemplary products including Myrj 45, 49, 52 and 53. Cremophor® are nonionic surfactants. Various commercially-available Cremophor® products include Cremophor EL, RH40, RH60 and RO. other exemplary nonionic surfactants include, but are not limited to, macrogol cetostearyl ether such as cetomacrogol 1000 and polyoxy 20 cetostearyl ether, macrogol 15 hydroxystearate, macrogol lauril ethers such as laureth 4 and lauromacrogol 400, macrogol monomethyl ethers, macrogol oleyl ethers such as polyoxyl 10 oleyl ether, macrogol stearates such as polyoxyl 40 stearate, menfegol nonoxinols such as nonoxinol-9, nonoxinol-10 and nonoxinol-11, octoxinols such as octoxinol 9 and oxtoxinol 10, polyoxamers such as polyoxalene, polyoxamer 188, polyoxamer 407, polyoxyl castor oil such as polyoxyl 35 castor oil, and polyoxyl hydrogenated castor oil such as polyoxyl 40 hydrogenated castor oil.

In some embodiments, compositions of the present disclosure further comprise at least one co-surfactant. As used herein the term "co-surfactant" refers to a substance added to, e.g., the preconcentrate in combination with the at least one surfactant to affect, e.g., increase or enhance, emulsification and/or stability of the preconcentrate, for example to aid in forming an emulsion. In some embodiments, the at least one co-surfactant is hydrophilic. In some embodiments, the at least one co-surfactant is not in free acid form. Examples of co-surfactants suitable for the present disclosure Include, but are not limited to, short chain alcohols comprising from 1 to 6 carbons (e.g., ethanol), benzyl alcohol, alkane diols and triols (e.g., propylene glycol, glycerol, polyethylene glycols such as PEG and PEG 400), glycol ethers such as tetraglycol and glycofurol (e.g., tetrahydrofurfuryl PEG ether), pyrrolidine derivatives such as N-methyl pyrrolidone (e.g., Pharmasolve®) and 2-pyrrolidone (e.g., Soluphor® P), and bile salts, for example sodium deoxycholate. Further examples include ethyl oleate, propylene glycol monolaurate (e.g., Lauroglycol®), diethylene glycol (e.g., Transcutol®). Other unlimiting list of polymers is presented in U.S. Pat. No. 10,391,060 to Pilgaonkar, incorporated herein by reference.

Another aspect of the present disclosure provides a method of preparing a self-nanoemulsifying drug delivery system (SNEDDS) 3D-printed tablet having glimepiride (GLMP), rosuvastatin (RSV) and/or pharmaceutically acceptable salts thereof, comprising the steps of: mixing curcuma oil, one or more surfactants and one or more co-surfactants, and water to form a first homogenous nanoemulsion; incorporating glimepiride (GLMP) and/or pharmaceutically acceptable salts thereof into the first homogenous nanoemulsion; mixing curcuma oil, one or more surfactants, one or more co-surfactants, and water to form a second homogenous nanoemulsion; incorporating rosuvastatin (RSC) and/or pharmaceutically acceptable salts thereof into the second homogenous nanoemulsion; mixing a gelling agent into the first and second homogenous nanoemulsions; blending one or more pharmaceutical excipients into the first and second homogenous nanoemulsions to form a first and second gel paste; loading the first and second gel paste into a 3D printer; and printing a multi-compartmentalized tablet.

In some embodiments, the one or more pharmaceutical excipients are 10-35 wt. %, preferably 12-30 wt. %, more preferably 15-25 wt. % of microcrystalline cellulose, 4-20 wt. %, preferably 6-15 wt. %, more preferably 8-12 wt. % of polyvinylpyrrolidone, 4-20 wt. %, preferably 6-15 wt. %, more preferably 8-12 wt. % of lactose, 1-16 wt. % preferably 2-14 wt. %, more preferably 3-8 wt. % of cellulose ethers and 1-16 wt. % preferably 2-14 wt. %, more preferably 3-8 wt. % of croscarmellose sodium. The homogenous nanoemulsion may include one or more co-surfactants that are selected from the group of polyethylene glycol (PEG), propylene glycol monolaurate, diethylene glycol, PEG 200, PEG 400, ethanol, isopropanol, butanol, pentanol. In some embodiments, the nanoemulsion may also include one or more surfactants selected from the group of polyoxyethylene sorbitan monooleate, sorbitan esters, nonionic polyoxyethylene, caprylocaproyl Polyoxyl-8 glycerides, and polyoxyethylated triglycerides castor oil. In some embodiments, the gelling agent is selected from polyacrylic acid (e.g., Carbopol®), xanthan gum, gelatin and HPMC.

The term "printing" described herein refers to the application of at least one printing formulation to a surface or a structure. Printing can use any appropriate device or method known in the art or later developed for a particular purpose. "3D printing" or "three-dimensional printing" refers to the printing of three-dimensional structures using appropriate printing technologies and printers as are known in the art. 3D printing is useful in the making of parts, products or layers using a computer driven, additive process, one or more layers at a time. 3D printing can build parts or other structures such as layers, using any appropriate material, such as, but not limited to plastic or metal, directly from CAD drawings or other digital images that have been preferably cross sectioned into many, if not hundreds or thousands of layers. 3D printing provides a faster and less costly alternative to machining, including but not limited to cutting, turning, grinding and drilling of materials, such as solid materials. Although various techniques are used in 3D printing in the relevant art, 3D printers use methods of additive fabrication, that is the building of a part or structure one layer at a time, with layers ranging in thickness from about a millimeter to less than $\frac{1}{1,000}$ of an inch. The building material can be in any appropriate form, such as, but not limited to a liquid, a powder or a sheet of material that is cured by heat, UV light, a chemical reaction or other appropriate method. As a non-limiting introduction to digital printing methods and devices, the following 3D printing methods may be used: fused deposition modeling (FDM), direct ink writing (DIW), stereolithography (SLA), laminated object manufacturing (LOM), and selective laser sintering (SLS) ink jet printing. As such, a plurality of 3D manufacturing and curing methods (e.g., thermal, photo, chemical catalysis, etc.) may be utilized based on the intended uses.

As used herein, the term "gel" or "gel-like" or "gel-matrix" refers to a gelatinous semisolid composition with a resilient consistency and yet a composition that exhibits no flow when in the steady-state. Unlike a liquid composition, a gel-like composition may have a definite shape depending on varying hardness of the gel structure. Upon 3D printing, the composition may harden to form a solid tablet or a gel tablet with sufficient rigidity as the liquid or gel-like 3D ink composition solidifies.

The 3D printed tablet may comprise additional pharmaceutically active agents encapsulated in the same or different compartments for varying drug-release rates to treat a subject in need thereof, for example a subject suffering multiple related pathogenic conditions such as cardiovascular, cancer, autoimmune disease and/or diabetes. The 3D printed multi-compartmentalized tablet may have two compartments for having glimepiride (GLMP) and/or rosuvastatin (RSV) in each compartment and may provide varying releasing rates. In some embodiments, the multi-compartmentalized tablet has 2, 3, 4, 5, 6, 7, 8, 9, 10, 11, 12 or more compartments for at least one active pharmaceutical ingredient. In some embodiments, the multi-compartmentalized tablet comprises multiple layers of coatings. The term "compartment", as used herein, refers to a section or volume in which the GLMP and/or RSV are divided into. The compartments are chambers, cavities, or pockets for holding active pharmaceutical ingredients and, in some embodiments, also may refer to solid or filled layers or sections of materials. In other embodiments, the multi-compartmentalized tablet is in a multi-layered shell shape. In preferred embodiments, the multi-compartmentalized tablet is not in a multi-layered shell shape where the active pharmaceutical ingredients are released from the core structure of the shell.

Figure 5A:
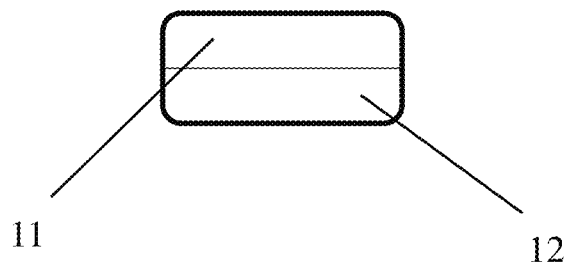
FIGS. 5A-D show exemplary multi-compartmentalized tablets of the present disclosure. (A) Two-compartment tablet with two layers, (B) two-compartment tablet with multiple layers, (C) three-compartment tablet with two layers, and (D) three-compartment tablet having multiple layers of 3D-printed active pharmaceutical ingredient-incorporated composition are shown.
Figure 5B:
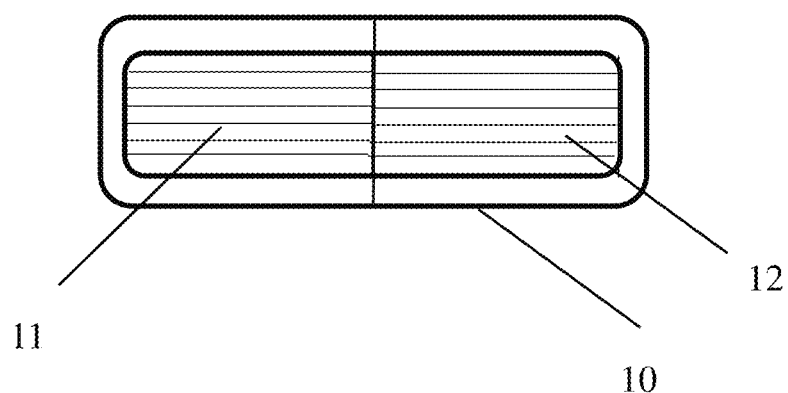
Figure 5C:
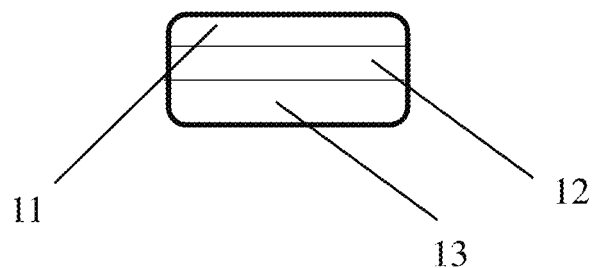
Figure 5D:
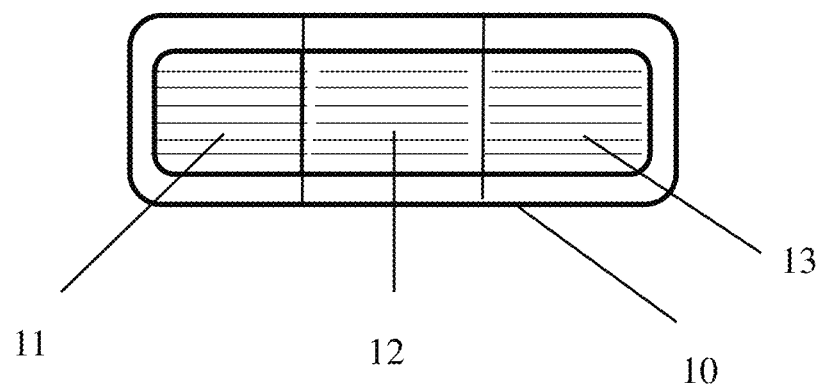

Referring to FIGS. 5A-D, exemplary two- or three-compartment 3D-printed tablets are described herein. In preferred embodiments, the tablet is a two-compartment tablet that has a bottom layer (i.e., compartment) 12 comprising GLMP and an upper layer 11 comprising RSV (FIG. 5A). Both layers are made of the same 3D ink components, but each layer includes different pharmaceutical ingredients. In some embodiments, the tablet is configured to include more than two layers. In other embodiments, all or partial surface of the tablet may be coated with other suitable materials. As noted above, the multi-compartment tablet may be in a multi-layered form (FIG. 5B). The outer surface layer 10 may either be the multi-layered tablet itself or an additional coating. In some embodiments, the multiple layers of the 3D-printing SNEDDS composition of the present disclosure are placed inside of the compartments 11, 12, 13. Alternatively, the multi-compartment tablet may be configured as a two-layered tablet, in which cases, the inner layer 11 and/or 12 is made of the 3D-printed SNEDDS composition that encapsulates one or more active pharmaceutical ingredients while the outer layer 10 being a coating layer.

In some embodiments, the 3D printed multi-compartmentalized tablet is a two-compartment tablet containing either glimepiride (GLMP) or rosuvastatin (RSV) in separate compartments. For example, a compartment 11 or 12 may encapsulate or incorporate glimepiride (GLMP) or rosuvastatin (RSV), but not both, and may have glimepiride (GLMP) and rosuvastatin (RSV) at a weight ratio of about 3:1 to 1:3. In such cases, each compartment 11 or 12 of the two-compartment tablet is configured to release glimepiride (GLMP) or rosuvastatin (RSV) at a different rate (FIG. 5A). In other embodiments, the two-compartment tablet comprises a combination of glimepiride (GLMP) and rosuvastatin (RSV) in the same compartment 11 or 12. In such cases, the two-compartment tablet is configured to release glimepiride (GLMP) and rosuvastatin (RSV) at the same rate from one compartment. Other multi-compartmentalized table configuration may also be contemplated, for example, three-compartment 3D-printed tablets (FIGS. 5C-D) having the same or different dosages or combinations of glimepiride (GLMP) and/or rosuvastatin (RSV) in the compartments 11, 12 and/or 13.

Another aspect of the present disclosure provides a method of treating a metabolic disorder or disease in a subject in need thereof by administering the 3D printed tablet to the subject in an amount sufficient to treat the metabolic disorder or disease, wherein the 3D printed tablet comprises glimepiride (GLMP), rosuvastatin (RSV) and/or pharmaceutically acceptable salts thereof; and 10-20 wt. % of curcuma oil in a self-nanoemulsifying drug delivery system (SNEDDS), wherein the 3D-printed tablet is a multi-compartmentalized tablet having at least one layer of GLMP and at least one layer of RSV in separate compartments, and wherein each compartment is configured to release GLMP or RSV at a different rate.

The term "subject" as used herein refers to a mammalian subject. Preferably, it is selected from a human, non-human animal, companion animal, non-domestic livestock or zoo animal. For example, the subject may be selected from a human, mouse, rat, dog, cat, cow, pig, sheep, horse, bear, and so on. In a preferred embodiment, said mammalian subject is a human subject. An effective amount of a composition of the present invention sufficient to achieve a therapeutic or prophylactic effect should be determined by standard procedures used by medical professionals, e.g., physicians. The compositions described herein may be administered on multiple occasions. The interval between single doses can be daily, weekly, monthly, or yearly. Alternatively, the composition can be administered as a sustained release formulation. As noted above, dosage and frequency will vary depending on a plurality of considerations including the intended uses (i.e., prevention or treatment), efficacy and the half-life of the composition in a subject. In the case of oral administration, the composition may be administered at a dose of 0.1 to 5 g/day, preferably 0.2 to 5 g/day, more preferably 0.4 to 3.0 g/day, and most preferably 0.6 to 2.0 g/day in 1 to 3 divided doses. However, the entire dose may be administered at once or in several divided doses. Subjects treated for a metabolic disorder can be administered the 3D-printed tablet according to the disclosure for 3, 6 or 9 months, or for 1 year, 2 years or more and can be administered the 3D-printed tablet in one, two or three dosage per day, or other multiple doses per day including 1 to about 10, 1 to 8, 1 to 6, 1 to 4 or 1 to 2 dosage units per day as appropriate for patient therapy. The term "dose unit" and "dosage unit" herein refer to a portion of a pharmaceutical composition that contains an amount of the 3D-printed tablet for a single administration to a subject. When orally administered at such dose, the administration period may be adequately determined depending on the target disease and degree of symptoms.

By a "therapeutically effective amount" is meant a sufficient amount of active agent to treat the disease or disorder at a reasonable benefit/risk ratio applicable to any medical treatment. It will be understood that the total daily usage of the compositions of the present invention will be decided by the attending physician within the scope of sound medical judgment. The specific therapeutically effective dose level for any particular subject will depend upon a variety of factors including the disorder being treated and the severity of the disorder; activity of the specific compound employed; the specific composition employed, the age, body weight, general health, sex and diet of the subject; the time of administration, route of administration, and rate of excretion of the specific compound employed; the duration of the treatment; drugs used in combination or coincidental with the specific active agent employed; and like factors well known in the medical arts. For example, it is well within the skill of the art to start doses of the compound at levels or frequencies lower than those required to achieve the desired therapeutic effect and to gradually increase the dosage or frequency until the desired effect is achieved. However, the daily dosage of the active agent may be varied over a wide range from 0.01 to 1,000 mg per adult per day. In particular, the compositions contain 0.01, 0.05, 0.1, 0.5, 1.0, 2.5, 5.0, 10.0, 15.0, 25.0, 50.0, 100, 250 and 500 mg of the active ingredient for the symptomatic adjustment of the dosage to the subject to be treated. A medicament typically contains from about 0.01 mg to about 500 mg of the active ingredient, in particular, from 1 mg to about 100 mg of the active ingredient. An effective amount of the drug is ordinarily supplied at a dosage level from 0.0002 mg/kg to about 20 mg/kg of body weight per day, especially from about 0.001 mg/kg to 7 mg/kg of body weight per day. As used herein, the term "about" refers to a range of values±10% of a specified value. For example, the phrase "about 200" includes ±10% of 200, or from 180 to 220.

The term "pharmaceutically acceptable salt" as used herein refers to the relatively non-toxic, inorganic and organic acid addition salts of compounds as described herein. These salts can be prepared in situ during the final isolation and purification of the compounds or by separately reacting the purified compound in its free base form with a suitable organic or inorganic acid and isolating the salt thus formed. Representative salts include the hydrobromide, hydrochloride, sulfate, bisulfate, nitrate, acetate, oxalate, valerate, oleate, palmitate, stearate, laurate, borate, benzoate, lactate, phosphate, tosylate, citrate, maleate, fumarate, succinate, tartrate, naphthylate mesylate, glucoheptonate, lactobsonate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to ammonium, tetramethylammonium, tetraethylammonium, methylamine, dimethylamine, trimethylamine, triethylamine, ethylamine, and the like (see, for example, Berge S. M, et al, "Pharmaceutical Salts," J. Pharm. Sci., 1977; 66:1-19 which is incorporated herein by reference.)

The terms "therapeutic agent", "medication" and "drug" are used herein interchangeably. The particulate delivery systems of the present invention may include therapeutic agents or drugs belonging to the therapeutic classes such as, but not limited to, anti-cancer agents, psychostimulants, antihistamines, expectorants, mucolytics, anti-tussive agents, serotonin and norepinephrine reuptake inhibitors, sympatholytics, antimuscarinics, PDE5 inhibitors, anti-Alzheimer's agent, analgesics, decongestants, analeptic agents, anesthetic agents, anti-asthmatics, anti-arthritic agents, anticholinergic agents, anti-convulsant agents, anti-depressant agents, antidiabetics, anti-helminthic agents, anti-diarrheal agents, anti-epileptics, anti-hyperlipidemic agents, antihypertensives, antihypotensives, peripheral vasodilators or vasoconstrictors, respiratory agents, anti-infective agents, anti-inflammatory agents, non-steroidal anti-inflammatory agents, anti-emetics, anti-migraine agents, anti-neoplastic agents, anti-tubercular agents, antibiotics, antacids, antiulcer agents, anti-Parkinsonism drugs, anti-pruritic agents, antipsychotic agents, antipyretic agents, anti-spasmodics, antiviral agents, anxiolytic agents, appetite suppressants, attention deficit hyperactivity disorder treating agents, cardiovascular agents, calcium channel blockers, antianginal agents, central nervous system agents, beta-blockers; antiarrhythmic agents, bronchodilators, central nervous system stimulants, diuretics, hormonolytics, hypercalcemics, hypoglycemic agents, immunosuppressive agents, beta-agonists, narcotic antagonists, nicotine, nutritional agents, parasympatholytics, antihemorrhoidals, psychotropics, sialagogues, steroids; sympathomimetics, tranquilizers; vasodilators, hypnotics, coronary dilators, calcium antagonists, chemotherapeutic drugs, antiprotozoan drugs, alkylating agents, mitotic inhibitors, anti-metabolites, plant alkaloids, terpenoids, taxanes, topoisomerase inhibitors, camptothecins, antitumour antibiotics, hormones, steroids, gonadotropin-releasing hormone agonists, estrogen receptor binding agents, farnesyl-protein transferase inhibitors, polyphenolic agents, cytoxics, multi-drug resistance modulators, radiosensitizers, antimanics, enkephalin analgesics, hallucinogenic agents, epidural and intrathecal anesthetic agents, general, local, regional neuromuscular blocking agents, sedatives, preanesthetics, anabolic steroids, dopamine agonists, growth hormone and analogs, hyperglycemic agents, lipid-altering agents, nutrients/amino acids, obesity drugs (anorectics), somatostatin, thyroid agents, vasopressin, vitamins, antiallergy, antiasthmatic agents, antiasthmatic agents (nonsteroidal), bronchoconstrictors, cough-cold-allergy preparations, corticosteroids, cathartics, cholelitholytic agents, gastrointestinal motility modifying agents, H2 receptor antagonists, irritable bowel syndrome agents, liver agents, metal chelators, gastric secretory agents, gastrointestinal drugs, drugs, pancreatitis agents, pancreatic enzymes, prostaglandins, sclerosing agents, anti-progestins, oxytocics, progestins, uterine-acting agents, anti-anemia drugs, anticoagulants, antifibrinolytics, antiplatelet agents, antithrombin drugs, coagulants, fibrinolytics, hematological agents, heparin inhibitors, blood drugs (e.g., drugs for hemoglobinopathies, hrombocytopenia, and peripheral vascular disease), anti-androgens, antigonorrheal agents, anti-resistant, antisepsis, dermatological agents, immunostimulatory agents, anthelmintic agents, antifungal, antimalarials, antimycobacterial, antiparasitic agents, antiprotozoal agents, radiopharmaceuticals, antitrichomonads, antituberculosis agents, chronic fatigue syndrome, anti-HIV drugs, anti-gout drugs, cyclooxygenase inhibitors, enzyme blockers, metalloproteinase inhibitors, counterirritants, antigingivitis agents, antiplaque agents, bactericidal agents, keratolytic agents, anti-acne agents, anti-androgenic agents, chelating agents, alpha adrenergic agonists/blockers, antivirals, beta adrenergic blockers, carbonic anhydrase inhibitors, immune system regulators, mast cell inhibitors, proteolytic enzymes, 5HT3 receptor antagonists, aldosterone receptor antagonists, alpha-glucosidase inhibitors, amebicides, aminoglycosides, androgens, angiotensin converting enzyme (ACE) inhibitors, angiotensin II inhibitors, anorexiants, anti-adrenergic agents, anti-hyperuricemic agents, antibacterials, anti-psoriatics, anti-rheumatics, antiseptic and germicides, bile acid sequestrants, bisphosphonates, chemokine receptor antagonists, chloride channel activators, cholesterol absorption inhibitors, cholesterol lowering agents, cholinergic agonists, cholinesterase inhibitors, contraceptives, cox-2 inhibitors, dipeptidyl peptidase 4 inhibitors, dopaminergic agents, factor Xa inhibitors, gamma-aminobutyric acid analogs, gamma-aminobutyric acid reuptake inhibitors, pain-modulating agents, glycoprotein platelet inhibitors, *H. pylori* eradication agents, histamine receptor antagonists, impotence agents, incretin mimetics, inotropic agents, ketolides, laxatives, leukotriene modifiers, meglitinides, metabolic agents, methylxanthines, mineralocorticoids, monoamine oxidase inhibitors, mTOR kinase inhibitors, muscle relaxants, neuraminidase inhibitors, norepinephrine-dopamine reuptake inhibitors, nucleoside reverse transcriptase inhibitors (NRTIs), non-nucleoside reverse transcriptase inhibitors (NNRTIs), peripheral opioid receptor antagonists, peripheral vasodilators, peripherally acting anti-obesity agents, prolactin inhibitors, protease inhibitors, proton pump inhibitors, psychotherapeutic agents, renin inhibitors, selective serotonin reuptake inhibitors, serotoninergic neuroenteric modulators, statins, anti-parasite agent, opioid, birth control agent, progestational agent, anti-glaucoma agent, ophthalmic agent, neurotoxin, muscle contractant, miotic agent, anti-secretory agent, anti-thrombotic agent, angiogenic agent, modulators of cell-extracellular matrix interactions (e.g., cell growth inhibitors and anti-adhesion molecules), anti-allergic agents, thrombin inhibitors, thrombolytics, tyrosine kinase inhibitors, anti-rheumatics, anti-thyroid agents, neuroleptics, cardiac inotropic agents, cough suppressants, cytotoxics, lipid regulating agents, nitrates and the like or combinations thereof may be employed.

In preferred embodiments, the tablet composition of the present invention (either empty composition or composition comprising a single or a combination of drugs) provides a tablet suitable for administered by the oral route (e.g., buccal, sublabial, sublingual, etc.). In addition, the 3D printed tablet may also be used topically, orally, rectally or vaginally, depending on the intended application. The 3D printed tablet maybe administered to prevent, slow the progression of, delay or treat a metabolic disorder of disease such as type 1 diabetes, diabetes mellitus, type 2 diabetes mellitus, impaired glucose tolerance, impaired fasting glucose, hyperglycemia, postprandial hyperglycemia, postabsorptive hyperglycemia, overweight, obesity, dyslipidemia, hyperlipidemia, hypercholesterolemia, hypertension, atherosclerosis, endothelial dysfunction, osteoporosis, chronic systemic inflammation, non-alcoholic fatty liver disease (NAFLD), retinopathy, neuropathy, nephropathy, polycystic ovarian syndrome, and/or metabolic syndrome. The use of 3D-printed tablet of the present disclosure may also include improving and/or maintaining glycemic control and/or for reducing of fasting plasma glucose, of postprandial plasma glucose, of postabsorptive plasma glucose and/or of glycosylated hemoglobin HbAlc; preventing, slowing, delaying or reversing progression from pre-diabetes, impaired glucose tolerance (IGT), impaired fasting blood glucose (IFG), insulin resistance and/or from metabolic syndrome to type 2 diabetes mellitus; preventing, reducing the risk of, slowing the progression of, delaying or treating of complications of diabetes mellitus such as micro- and macrovascular diseases, such as nephropathy, micro- or macroalbuminuria, proteinuria, retinopathy, cataracts, neuropathy, learning or memory impairment, neurodegenerative or cognitive disorders, cardio- or cerebrovascular diseases, tissue ischemia, diabetic foot or ulcus, atherosclerosis, hypertension, endothelial dysfunction, myocardial infarction, acute coronary syndrome, unstable angina pectoris, stable angina pectoris, peripheral arterial occlusive disease, cardiomyopathy, heart failure, heart rhythm disorders, vascular restenosis, and/or stroke; reducing body weight and/or body fat and/or liver fat and/or intra-myocellular fat or preventing an increase in body weight and/or body fat and/or liver fat and/or intra-myocellular fat or facilitating a reduction in body weight and/or body fat and/or liver fat and/or intra-myocellular fat; preventing, slowing, delaying or treating the degeneration of pancreatic beta cells and/or the decline of the functionality of pancreatic beta cells and/or for improving, preserving and/or restoring the functionality of pancreatic beta cells and/or stimulating and/or restoring or protecting the functionality of pancreatic insulin secretion; preventing, slowing, delaying or treating non alcoholic fatty liver disease (NAFLD) including hepatic steatosis, non-alcoholic steatohepatitis (NASH) and/or liver fibrosis (such as e.g. preventing, slowing the progression, delaying, attenuating, treating or reversing hepatic steatosis, (hepatic) inflammation and/or an abnormal accumulation of liver fat); preventing, slowing the progression of, delaying or treating type 2 diabetes with failure to conventional antidiabetic mono- or combination therapy; achieving a reduction in the dose of conventional antidiabetic medication required for adequate therapeutic effect; reducing the risk for adverse effects associated with conventional antidiabetic medication (e.g. hypoglycemia or weight gain); and/or maintaining and/or improving the insulin sensitivity and/or for treating or preventing hyperinsulinemia and/or insulin resistance.

Example 1

Methods and Materials for Manufacturing SNEDDS 3D Printed Tablet

Glimepiride and Rosuvastatin were kindly gifted by the Saudi Pharmaceutical Industries & Medical Appliances Corporation (SPIMACO) (Alqasim, Saudi Arabia) and the Saudi Arabian Japanese Pharmaceuticals Co. Ltd (SAJA) (Jeddah, Saudi Arabia), respectively. Microcrystalline cellulose (Avicel) PH-101 from Winlab laboratory chemicals (Leicestershire, UK). Hydroxypropyl methyl cellulose (HPMC) 4000 cp were obtained from Spectrum Chemical Manufacturing Corporation (Gardena, Calif.). Lactose anhydrous, Polyethylene glycol (PEG) 400, Tween 80, Polyvinyl pyrrolidone (PVP) with a molecular weight of 360,000 Da (K90), Methocel® A15 LV, 27.5-31.5% methoxyl basis were all purchased from Sigma-Aldrich Inc. (St. Louis, Mo.). Croscarmellose sodium (Ac-di-sol) from Biosynth International, Inc (San Diego, Calif.).

Plant Material and Oil Extraction

*Curcuma longa linn* (Turmeric) rhizomes (Zingiberaceae) were obtained from a local market in Jeddah, Saudi Arabia. The plant's authentication was established by Dr. Emad Al-Sharif, Professor of Plant Ecology, Faculty of Science & Arts, King Abdulaziz University, and a voucher specimen (no. CL1442) was kept in the herbarium at Faculty of Pharmacy, KAU. The dried rhizomes (3.5 kg) were grinded and extracted with n-hexane (8 L×6) at room temperature. The solvent was distilled off under reduced pressure below 50° C. to yield an orange yellow odoriferous viscous oil (45 g).

Development of Curcuma Oil Based SNEDDS

The oil of *Curcuma longa* ($X_1$) was used to develop different SNEDDS formulations utilizing tween 80 ($X_2$) and PEG 400 ($X_3$) as surfactant and co-surfactant, respectively. Mixture design of extreme vertices was used to develop SNEDDS with minimum globule size using the statistical package Statgraphics® Centurion XV Software, Version 15.2.05 StatPoint Technologies, Inc. (Warrenton, Va., USA). A total of thirteen runs were performed. Each run contains a specified weight percentage of the three components that was always added to 100%. The composition of the SNEDDS formulation is illustrated in Table 1. Briefly, 1 g of each SNEDDS formulation was prepared in a screw cap vials by accurately weighing the specified amount of each component. Each formulation mixture was vortex for 60 s to get a homogenous dispersion.

Known weight of each formulation was added to a specified volume of distilled water, in a ratio of 1:10 (w/v), on a magnetic stirrer until a homogenous yellowish nanoemulsion was obtained. Malvern Zetasizer Nano ZSP, Malvern Panalytical Ltd. (Malvern, United Kingdom) was used to evaluate the size and polydispersity index of the prepared nanoemulsion.

Data obtained for the globule size of the prepared SNEDDS formulated were analyzed using the Statgraphics software. The optimized SNEDDS formulation, with the minimum size, was identified. This formulation was prepared and characterized as mentioned above.

TABLE 1

Composition of SNEDDS formulations according to the extreme vertices mixture design and their globule size.

| Run | $X_1$ (%) | $X_2$ (%) | $X_3$ (%) | Globule size (nm) Observed | Fitted |
|---|---|---|---|---|---|
| 1 | 15.0 | 30.0 | 55.0 | 105.0 | 103.44 |
| 2 | 15.0 | 10.0 | 75.0 | 93.0 | 92.31 |
| 3 | 25.0 | 20.0 | 55.0 | 359.0 | 355.01 |
| 4 | 25.0 | 10.0 | 65.0 | 313.0 | 306.84 |
| 5 | 17.5 | 23.75 | 58.75 | 157.0 | 156.95 |
| 6 | 17.5 | 13.75 | 68.75 | 144.0 | 140.92 |
| 7 | 22.5 | 18.75 | 58.75 | 279.0 | 272.67 |
| 8 | 22.5 | 13.75 | 63.75 | 251.0 | 254.19 |
| 9 | 15.0 | 20.0 | 65.0 | 123.0 | 126.03 |
| 10 | 20.0 | 25.0 | 55.0 | 233.0 | 238.56 |
| 11 | 20.0 | 10.0 | 70.0 | 196.0 | 200.69 |
| 12 | 25.0 | 15.0 | 60.0 | 295.0 | 305.94 |
| 13 | 20.0 | 17.5 | 62.5 | 205.0 | 199.45 |

Abbreviations:
$X_1$, curcuma oil;
$X_2$, tween 80;
$X_3$, Polyethylene glycol 400.

Example 2

Preparation of SNEDDS Paste Formulation

Two types of viscous gel matrix formulations were prepared using HPMC (4% w/v) as a gelling agent. Pure gel and SNEDDS-based gel formulations were prepared according to the formulation composition depicted in Table 2. Pure gel formulations were prepared by dispersing a known weight of either RSV or GLMP in distilled water over a magnetic stirrer. HPMC was added gradually to the mixture while stirring. The obtained medicated polymeric mixture formulations were left for overnight at 4° C. in a refrigerator to allow complete swelling of the HPMC particles and formation of viscous gels.

SNEDDS-based gels were prepared by adding known weight of either RSV or GLMP to 2 g of the prepared optimized SNEDDS formulation. The medicated SNEDDS formulation was added to 18 mL of distilled water over a magnetic stirrer. HPMC was added gradually to mixture with continuous stirring. The medicated polymeric mixture was left over night in the refrigerator. Non-medicated (drug free) SNEDDS-based gel matrix formulation was also prepared.

Powder mixtures of Avicel (20 wt. %), PVPK90 (10 wt. %), lactose (10 wt. %), methocel (5 wt. %) and Ac-Di-Sol (5 wt. %) were well-blended and transferred to a mortar containing the prepared gel matrix. Mixing of the ingredients was continued until a smooth homogenous paste was obtained. PVPK90, lactose and methocel were used as soluble tablet ingredients. Avicel was used as insoluble ingredient and Ac-Di-Sol was used as a disintegrant.

Rheological Characterization of the SNEDDS Formulation

A Kinexus rotational rheometer (Malvern Instruments Ltd. Worchestershire, UK) was utilized to investigate the rheological behavior of the prepared formulations (F1-F6) using the rSpace software package which controls the apparatus and permits sample measurement and analysis. The machine is equipped with two parallel plates where the sample is placed between the top and bottom plate to perform the rheological tests. A freshly prepared formulation was mounted carefully to the middle of a Peltier temperature-controlled bottom plate. Subsequently, the rheometer's upper plate was lowered to a predetermined position to create a 1 mm gap between the upper and lower plates. Excess sample was removed from the upper plate rheometer's margins. Measurement was made and data collected and analyzed appropriately. The relation between viscosity and shear rate, and that between shear stress and shear rate versus time were investigated.

TABLE 2

Composition and characteristics of the prepared hydrogel pastes and the 3D-printed tablets.

| | F1 | F2 | F3 | F4 | F5 | F6 |
|---|---|---|---|---|---|---|
| Drug | — | GLMP | RSV | GLMP | RSV | GLMP and RSV |
| Vehicle | SNEDDS in DW | DW | DW | SNEDDS in DW | SNEDDS in DW | SNEDDS in DW |
| Viscosity (Pa · s) | 6550 ± 278 | 8604 ± 295 | 9185 ± 153 | 6648 ± 135 | 6684 ± 451 | — |
| Weight before drying (mg) | 1003.33 ± 31.32 | 965.46 ± 46.55 | 983.75 ± 84.29 | 1053.53 ± 55.84 | 1017.14 ± 61.69 | 2095.11 ± 167.56 |
| Weight after drying (mg) | 532.58 ± 23.7 | 490.53 ± 27.76 | 498.88 ± 55.32 | 541.68 ± 61.02 | 559.39 ± 41.45 | 1067.54 ± 77.32 |
| Thickness (mm) | 3.035 ± 0.038 | 2.647 ± 0.160 | 2.826 ± 0.228 | 3.239 ± 0.178 | 2.876 ± 0.128 | 5.797 ± 0.156 |
| Diameter (mm) | 14.656 ± 0.148 | 13.289 ± 0.485 | 15.201 ± 0.228 | 14.855 ± 0.319 | 14.082 ± 0.249 | 14.342 ± 0.109 |
| Friability (%) | 0.068 | 0.159 | 0.199 | 0.117 | 0.043 | 0.089 |
| Drug content (mg) | — | 3.98 ± 0.201 | 9.76 ± 0.359 | 3.918 ± 0.219 | 9.691 ± 0.594 | 4.052 ± 0.087 and 9.711 ± 0.097 |

Abbreviations: GLMP, glimepiride; RSV, rosuvastatin, SNEDDS, self-nanoemulsifying drug delivery system; DW, distilled water;

Notes: The concentrations of GLMP and RSV in the prepared tablets were 4 and 10 mg, respectively. Avicel (20 wt. %), PVPK90 (10 wt. %), lactose (10 wt. %), methocel (5 wt. %) and Ac-Di-Sol (5 wt. %) were added to all formulations. F6 was printed using equal amounts of F4 and F5.

Manufacturing of the 3D-Printed Tablet

The prepared paste formulations were developed into 3D-printed tablets using a REGEMAT3D V1 BioPrinter (REGEMAT Inc. Granada, Spain). A cylinder of 15 mm diameter and 5.6 mm height, assuming a total of eight layers each of 0.7 mm layer thickness, were designed using a computer-aided design (CAD) modelling software (REGEMAT 1.4.9 Designer). The prepared pastes were freshly prepared and loaded separately into a printing extrusion tool (5 cc) for extrusion of tablets through a 0.58 mm printing nozzle with a flow speed of 2.6 mm/s and infill speed of 10 mm/s. The printing nozzle was set to move in a vertical and horizontal directions to place the paste in the selected area of the building plate. The printing process was done layer-by-layer for building the 3D-printed tablet structure. The average time needed to complete the printing process for each tablet was 10 minutes. The printed tablets were placed in a vacuum dryer at 40° C. for 24 hours for complete drying and finally stored in a hermetically sealed container. Tablets of formulation six "F6" were printed using equal amounts of F4 and F5 pastes. The concentration of GLMP and RSV in this formulation can be modified according to the personal need.

Example 3

Characterization of the 3D Printed Tablets

The prepared dried 3D-printed tablets (F1-F6) were characterized for weight, thickness, diameter, friability, drug(s) content and in vitro drug release. All tests were conducted according to the requirements stated in the United States Pharmacopeia for quality control tests of tablets (USP 41-NF 36, 2018). The average weight of ten tablets, from each formulation, was estimated using Mettler Toledo AJ100, electric balance (Greifensee, Switzerland). The thickness and diameter (n=10) were determined using Mitutoyo dial thickness gauge (Kawasaki, Japan). Friability (n=10) of the prepared tablets was evaluated using Erweka Friabilator type PTF1, Pharma-test (Hainburg, Germany). It was calculated as a fraction of the weight of the original tablets after allowing the studied tablets to rotate in the test apparatus for 4 min at 25 rpm.

Spectrophotometric Analysis of GLMP and RSV

For the quantification of GLMP or RSV and a combination of both in the studied tablets, a simple spectrophotometric method has been used as previously described with a modification (Afroz et al., 2011). Two separate stock solutions (100 µg/ml) of GLMP and RSV were prepared in 0.1 N NaOH solution. Working standard solutions containing series of known concentrations for each drug were prepared in the range 2-25 µg/ml by diluting the prepared drug stock solution with 0.1 N NaOH solution. Also, combined standard solutions of GLMP in the range 10-20 µg/ml that all contain 10 µg/ml of RSV were prepared. Finally, combined RSV standard solutions (10-20 µg/ml) that were spiked with 10 µg/ml of GLMP were also prepared.

Standard solutions of either RSV or GLMP containing 10 µg/ml drug were scanned separately in the ultraviolet (UV) range 200-400 nm, using UV-Vis spectrophotometer UV-2600, Shimadzu Corporation (Kyoto, Japan), to identify the maximum wavelength for each drug. GLMP and RSV showed a maximum absorbance at 228 nm and 241 nm, respectively. The absorbances of the prepared GLMP standard solutions were recorded at 228 nm, while that of RSV were measured at 241 nm. A standard calibration curve that relates the absorbance and the concentration was constructed and the equation of the line which fits to the data (Equation 1) was generated for each drug. The absorptivity values for GLMP and RSV were determined. Simultaneous equation method was used to estimate the concentration of both drugs in the prepared combined standard solutions and in the pharmaceutical formulations using Equations 2 and 3.

$$Y = mX + b \qquad \text{Equation 1}$$

$$\text{Concentration of RSV} = (A_2 ay_1 - A_1 ay_2)/(ax_2 ay_1 - ax_1 ay_2) \qquad \text{Equation 2}$$

$$\text{Concentration of GLMP} = (A_1 ax_2 - A_2 ax_1)/(ax_2 ay_1 - ax_1 ay_2) \qquad \text{Equation 3}$$

Where "Y" is the absorbance, "X" is the concentration, "m" is the slope of the line, "b" is the intercept, $A_1$ is the absorbance of the sample at 241 nm, $A_2$ is the absorbance of the sample at 228 nm, $ax_1$ is the absorptivity of RSV at 241 nm, $ax_2$ is the absorptivity of RSV at 228 nm, $ay_1$ is the absorptivity of GLMP at 241 nm and $ay_2$ is the absorptivity of GLMP at 228 nm.

Drug Content and In-Vitro Release

The concentration of GLMP in F2 and F4 tablet formulations, and the concentration of RSV in F3 and F5 tablet formulations were determined by placing separately five tablets from each formulation in a glass bottles containing 100 ml of 0.1 N NaOH. The bottles were left overnight in a shaking water bath, Model 1031; GFL Corporation (Burgwedel, Germany), at 25° C. The content of each bottle was thoroughly homogenized using UltraTurax, IKA® T18 basic Homogenizer (Campinas, Brazil) for 10 minutes and subjected to filtration through filter paper. The filtrate was further diluted and the concentration of GLMP or RSV was determined spectrophotometrically, against blank of F1, using equation 1 for the best line of fit for each drug. Tablets of F6 were also subjected to the same procedure except that the concentration of both drugs was determined using the simultaneous equations 2 and 3.

The in vitro drug release of the prepared 3D-printed tablet formulations was studied using the paddle type USP dissolution test apparatus (type II), DT 700 LH device, Erweka GmbH DT 700 (Heusenstamm, Germany). The test was carried out in 900 ml of distilled water containing 0.1% sodium lauryl sulfate at 37° C. The paddle speed was adjusted at 75 rpm. Samples of 5 ml, with immediate replacement, were withdrawn at 0.25, 0.5, 1, 2, 3, 4, 5, 6 and 12 h. The collected samples were filtered and assayed for drug(s) content, against blank of F1, as discussed above. Profiles for the drug release were constructed. The experiment was conducted in triplicate.

Scanning Electron Microscope (SEM)

To inspect inner and surface structures of the prepared 3D-printed tablets, SEM images for SNEDDS loaded tablets and those prepared without SNEDDS were taken. Tablet formulations F1 and F2 were used in this study utilizing Philips XL30 SEM (Eindhoven, Netherlands). Samples from the studied tablet surface and inner layers were prepared using a surgical scalpel. The prepared samples were mounted onto aluminum stubs and sputter-coated with gold. Images were taken at accelerating voltage of 10 kV.

Many researches have reported the effect of the bioactive constituents extracted from *Curcuma longa* on the treatment of inflammation, neurodegenerative disorders, cancer and diabetes (Nabavi et al., 2015; Oliveira et al., 2020; Parsamanesh et al., 2018). Activation of immune response, antibacterial and antiviral effects, anthelminthic, anti-Alzheimer, antioxidant and antinociceptive activities were also mentioned (Arshami et al., 2013; Liju et al., 2011). There is also an increasing interest in curcuma oil for its protective role in cardiovascular disorders through its effect in decreasing the blood total cholesterol and low-density lipoprotein (Kim & Kim, 2010). Accordingly, we aimed to prepare curcuma oil-based SNEDDS formulation that is characterized by a smaller globule size subsequently mixed with the suitable tablet excipients and a gel matrix agent to develop a medicated pastes. GLMP and/or RSV were added to the formulations to investigate its usefulness in developing a solid oral dosage form characterized by utilizing the 3D-printing technology. The pharmacokinetic of GLMP and/or RSV, and the beneficial combination of curcuma oil-based SNEDDS with both drugs on the hypoglycemic and hypolipidemic activities.

During SNEDDS development, tween 80 and PEG were used as a surfactant and co-surfactant, respectively as both have been utilized in our previously published work during the preparation of SNEDDS with different oils such as sefsol, linoleic acid, olive oil, oleic acid and isopropyl myristate (Abdallah et al., 2021; Ahmed et al., 2014; El-Say et al., 2015).

Optimization of Curcuma Oil Loaded SNEDDS Formulation.

In some embodiments, thirteen SNEDDS formulations were examined. The order of the experimental runs has been fully randomized to provide protection against the effects of lurking variables. Different models are available to fit the data, which include the linear, quadratic, special cubic and the cubic model. The linear model consists of first-order terms for each of the components. The quadratic model adds cross-products between pairs of components. The special cubic model adds terms involving products of three components. The cubic model adds other third-order term. Each model is shown with a P-value which tests whether that model is statistically significant when compared to the mean square for the term below. Normally, we would select the most complicated model with a P-value less than 0.05, with assumption that the data represents a 95.0% confidence level. According to this criterion, it appears that the special cubic model (P-value=0.0158) is adequate for the data. The quadratic and cubic models showed P-values of 0.3457 and 0.5684, respectively. The currently selected model is the cubic model.

Analysis of variance (ANOVA) for the currently selected cubic model revealed that the P-value for this model is less than 0.05, and there is a statistically significant relationship between globule size and the components at the 95.0% confidence level. The R-Squared statistic indicates that the model as fitted explains 99.62% of the variability in globule size. The adjusted R-squared statistic, which is more suitable for comparing models with different numbers of independent variables, is 98.48%. The equation of the fitted model is $$\text{Globule size} = -62.2901 X_1 + 103.444 X_2 + 92.3094 X_3 + 1337.7 X_1 X_2 + 1167.31 X_1 X_3 + 112.612 X_2 X_3 - 2582.93 X_1 X_2 X_3 + 792.224 X_1^2 X_2^2 + 766.274 X_1^2 X_3^2 + 7.99058 X_2^2 X_3^2$$

Figure 1B:
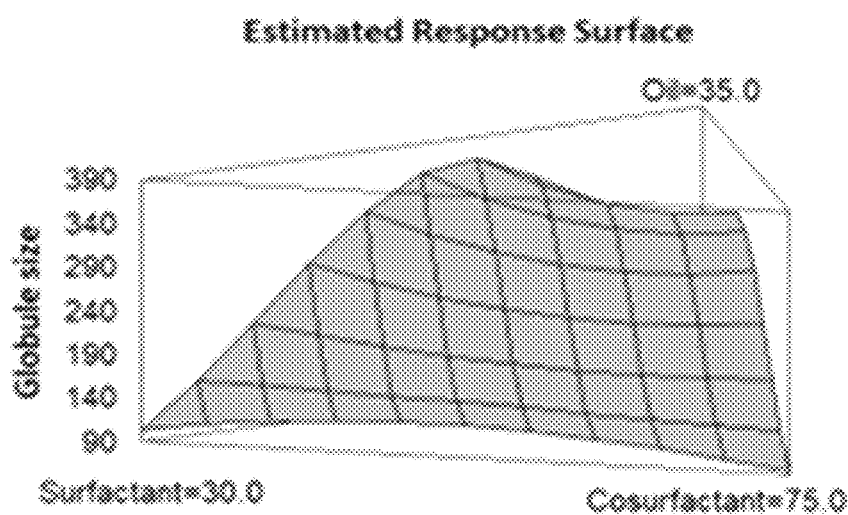

Contour and estimated response surface plots that demonstrate the effect of oil, surfactant and co-surfactant on the globule size were constructed and are illustrated in FIGS. 1A-B. In these plots, the studied components are located at the corners and globule size that achieve values in the range of 90-360 nm is represented. The combination of factor levels which minimizes the particle size and achieve a globule size of 92.32 nm were found to be; 15%, 10% and 75% for oil, surfactant and co-surfactant, respectively. An optimized SNEDDS formulation that contains these levels was prepared and characterized for globule size and the observed value was found to be 94.43±3.55 nm.

Preparation and Characterization of SNEDDS-Loaded Paste

Following the development of the optimized SNEDDS, two different types of pastes were studied. SNEDDS-loaded pastes and pure pastes formulations. GLMP and/or RSV were added to develop 3D-printed formulations used in treatment of diabetes and/or hyperlipidemia. HPMC hydrogel was used as a binder for the selected tablet excipients to form viscous pastes. The solid content namely; avicel, PVPK90, lactose, methocel, Ac-Di-Sol and the studied drug(s) constituted more than 50% of the total paste weight which accounts for the marked shrinkage and reduction in tablet weight after drying as illustrated in Table 2. This finding is in a good agreement with the previous works that reported bigger wet tablets which underwent significant shrinkage upon drying (Khaled et al., 2015; Zidan et al., 2019). Various trials containing lower concentrations of avicel, lactose and PVP were initially screened but resulted in a less intact tablets that exhibited marked deformations in shape after printing. The percentages of avicel and lactose used were kept at the minimum level that allow microextrusion 3D-printing process under low pressure. Zidan et al studied a concentrations of 10-30 wt. % and 13-60 wt. % for lactose and avicel, respectively during 3D-printing of modified release tablets containing diclofenac sodium (Zidan et al., 2019). They reported that pastes containing high content of avicel (about 60 wt. %) required high extrusion pressure. Also, they mentioned that the aqueous solubility, hygroscopicity and/or swelling of the excipients are parameters that affect the 3D-printing process.

During the printing process, all the studied pastes were extruded from the same nozzle (0.58 mm) at an optimum flow speed of 2.6 mm/s. Lower flow speed did not allow continuous deposition of the tablet layers while, higher flow speed did not permit good construction of an intact tablet layers as there was not enough time for the printed layer to dry. The studied nozzle size allows for free flowing of the pastes at the adjusted flow speed. Previous reports indicated that the nozzle size is significantly affecting the flow index rather than the consistency of the paste. Rahman et al. and Zhang et al. mentioned that narrow orifice resulted in a low flow, which increased the applied flow pressure while wider nozzle orifice (0.6 mm) enhanced the flow (Rahman et al., 2002; Zhang et al., 2011).

Figure 2:
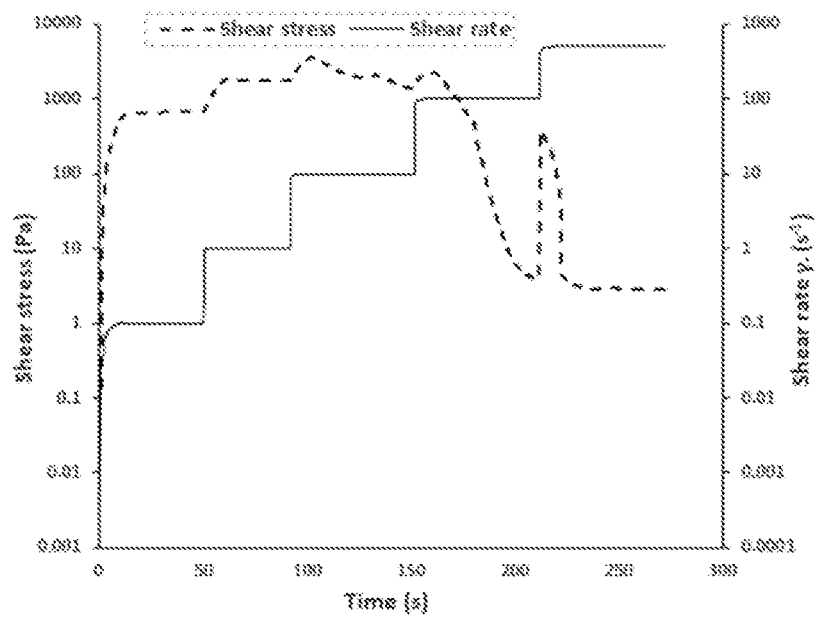
FIG. 2 shows rheological characterization of SNEDDS-based paste formulation (top) and pure paste formulation (bottom) exhibiting shear-thinning behavior.
Figure 2:
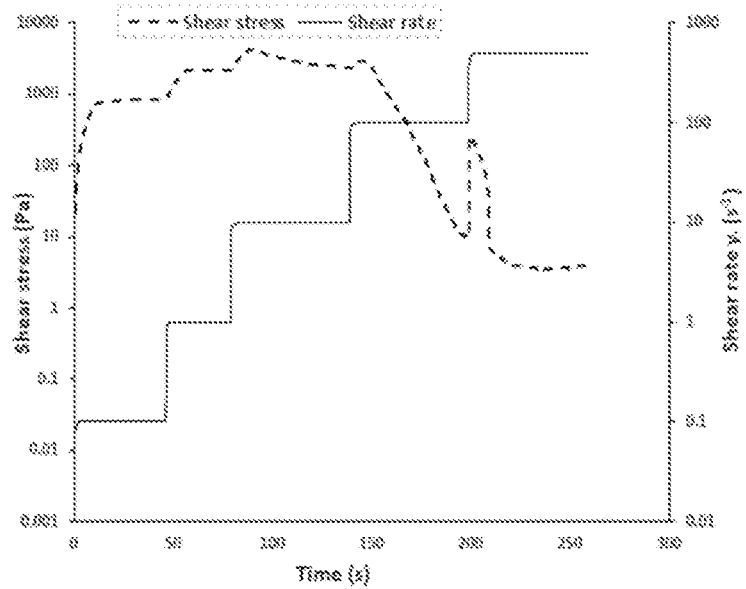

Rheological characterization of the prepared pastes indicated that all of the studied pastes exhibited shear-thinning behavior (FIG. 2). All the studied pastes exhibited a pseudoplastic behavior with a value of flow index "n" less than 1. The obtained results for the rheological behavior of our pastes are in a good agreement with previous work for carbopol based 3D-printing pastes (Zidan et al., 2019). It is noted that during the printing process using REGEMAT3D V1 BioPrinter, the printing pressure was unaltered during the extrusion process while only the flow rate was adjusted. Viscosity values of the prepared pastes are represented in Table 2. SNEDDS-based pastes illustrated lower viscosity than the corresponding pure paste formulations, the effect that could be attributed to the presence of SNEDDS components (oil, PEG and tween 80) that lubricate the solid particles and prevent water loss. Both types of pastes exhibited almost similar flow and rheological behavior except for the slight changes due to the existence of SNEDDS as illustrated in FIG. 2. Addition of the drug, either GLMP or RSV, insignificantly changed the viscosity value of non-medicated paste (F1) by about 1.5% and 2.05% in F4 and F5, respectively.

Development and Characterization of 3D-Printed Tablets

Figure 3:
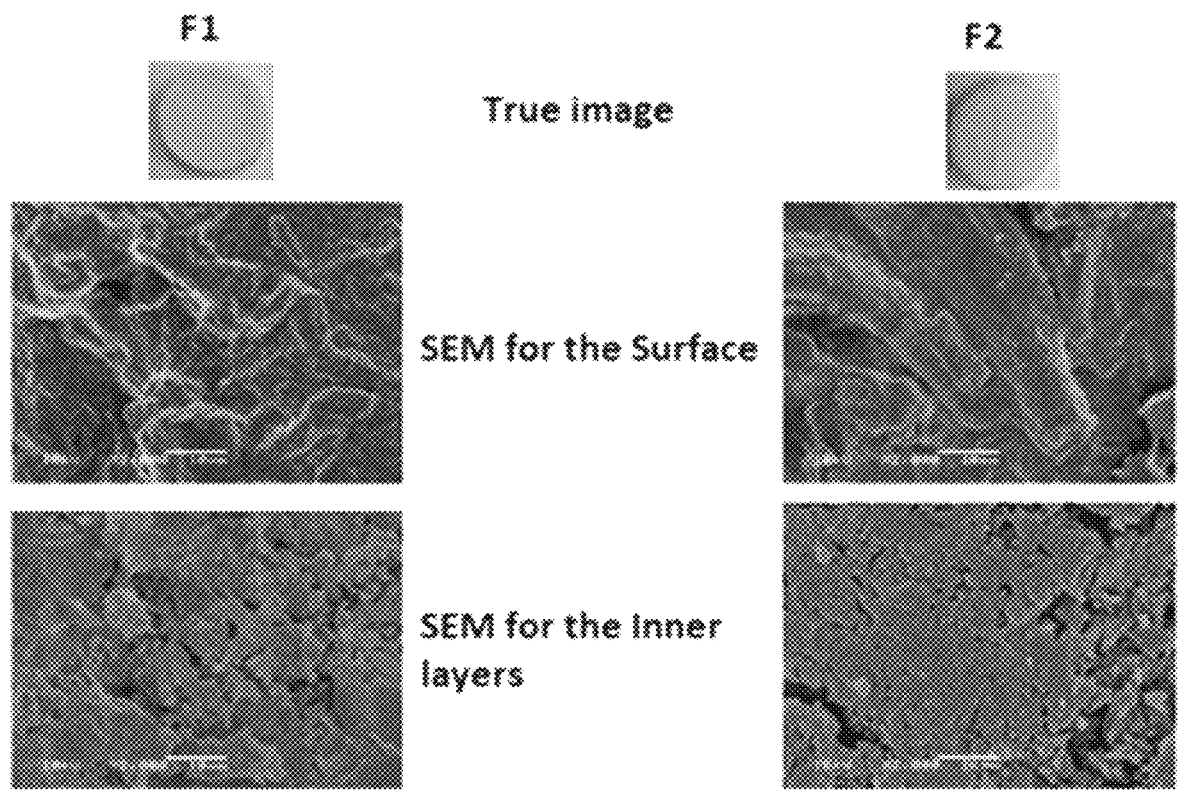
FIG. 3 shows images for the dried tablet formulations containing either SNEDDS-based paste (F1) or pure paste (F2).

During development of the 3D-printed tablet formulation, avicel and anhydrous lactose were used as diluents, PVPK90 as a binder and Ac-Di-Sol as a disintegrant. All the prepared tablet formulations were printed utilizing a CAD modelling software (REGEMAT 1.4.9 Designer). Images for the dried tablet formulations containing either SNEDDS-based paste (F1) or pure paste (F2) are illustrated in FIG. 3. All of the prepared tablets were printed through a cylinder of 15 mm diameter. Eight layers were used during the printing process of all the studied formulations except for F6 that was printed utilizing eight layers of F4 and the eight layers of F5. After printing, the tablets were kept in a vacuum dryer at 40° C. for 24 hours to allow fusion of the layer and complete drying of the tablets. The dried tablets maintained their original shape except for the decrease in the thickness and weight and a tiny change in the diameter due to water evaporation from the formulation that leads to shrinkage in the prepared tablets. Table 2 depicts the weight, thickness, diameter, friability, and drug content of all the prepared dried tablets. Friability was less than 1% which is an indication of the good mechanical strength. Tablets were prepared using 4 mg and 10 mg of GLMP and RSV, respectively which are comparable to the marketed products. The dried tablets showed a drug content of 3.918±0.219-4.052±0.087 and 9.691±0.594-9.76±0.359 for GLMP and RSV, respectively. Tablets of formulation F6 were prepared using a combination of GLMP and RSV. The concentration of both drugs can be changed according to the personal need by changing the amount of the paste (number of layers) used during printing of the tablet.

Figure 4A:
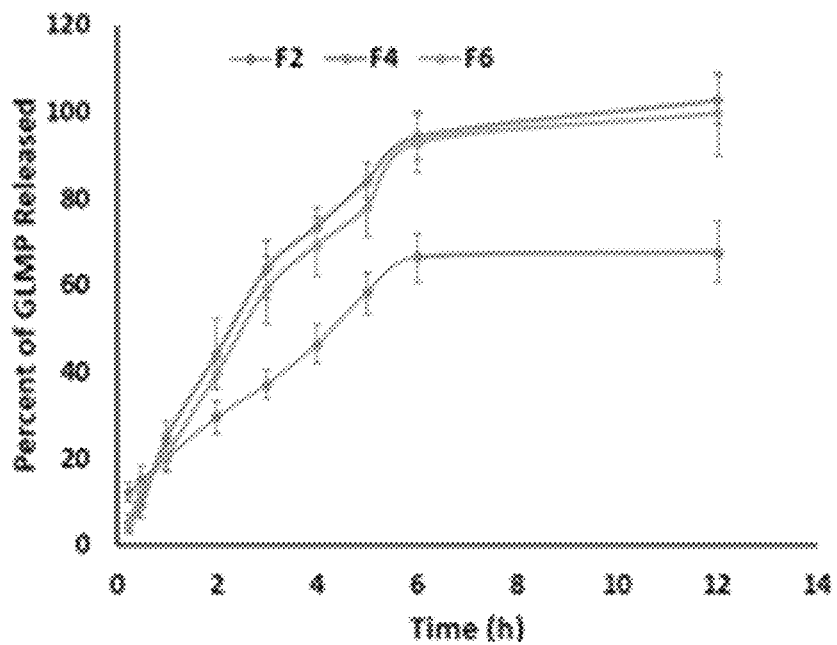
FIGS. 4A-B show the in vitro release profiles of (A) GLMP and (B) RSV in the prepared tablet formulations.
Figure 4B:
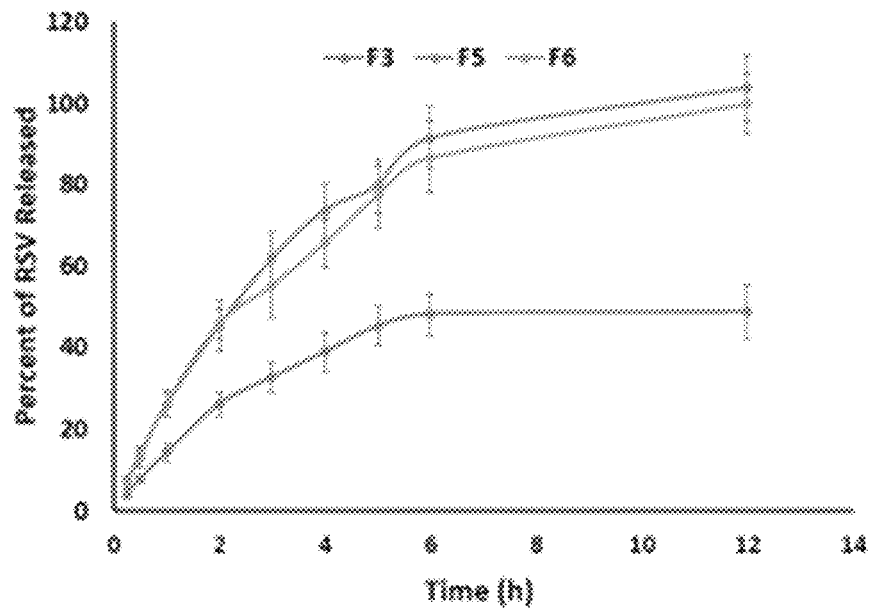

The in vitro release profiles of the prepared tablet formulation (F2-F6) are represented in FIGS. 4A-B. All the studied formulation showed an extended drug release behavior. The release from the drug loaded SNEDDS-based tablet formulations was superior to that of the corresponding pure drug loaded tablets. This effect could be attributed to the small size of the drug loaded SNEDDS in formulations F4 and F6 for GLMP and formulations F5 and F6 for RSV which provided large surface area for the release of both drugs.

Scanning Electron Microscope (SEM) Image Analysis

SEM images of both tablets' formulations revealed that no crystals were observed on the tablet surface (FIG. 3). The surface of both tablet formulations was less porous and exhibited some curvature with the appearance of tortuosity which may occur during fusion and solidification of the layers. The surface of SNEDDS-based tablet formulation was more homogenous and less porous which may be due to the presence of the SNEDDS formulation that render the paste more consistent and decreased the rate of water evaporation during the drying step. The inner structure of the F2 tablet showed a dried interlocking flakes like structure with some void spaces and pores, as previously reported for HPMC based sustained release matrix tablets (Roy et al., 2012). F1 tablet illustrated a non-uniform gel like structure with a smaller number of void and pores which may be due to the incorporation of SNEDDS that makes the matrix more wet and decrease the rate of water loss. Accordingly, in this study we developed oral 3D printed tablet formulations containing GLMP and/or RSV. The prepared formulations showed good quality attributes and were able to release the drug(s) in a controlled release manner.

Curcuma oil was successfully extracted and used to develop an optimized SNEDDS formulation of globule size 94.43±3.55 nm utilizing tween 80 and PEG 400 as a surfactant and co-surfactant, respectively. Pastes contain either pure or SNEDDS-based HPMC gel matrix were 3D printed. Rheological characterization of the prepared pastes showed a pseudoplastic shear thinning behavior. Tablets contain GLMP and/or RSV were developed utilizing a 3D BioPrinter using 0.58 mm nozzle and a flow speed of 2.6 mm/s. A simultaneous equation method was used to estimate the drug concentration in F6 tablet formulation which was developed to contain 4 mg and 10 mg of GLMP and RSV, respectively. The release of the studied drugs was higher from the SNEDDS containing tablets. The concentration of GLMP and RSV could be changed in the prepared tablets according to the personal need.

REFERENCES FOR EXAMPLES 1-3

Abdallah, H. M., El-Bassossy, H. M., El-Halawany, A. M., Ahmed, T. A., Mohamed, G. A., Malebari, A. M., & Hassan, N. A. (2021). Self-Nanoemulsifying Drug Delivery System Loaded with *Psiadia punctulata* Major Metabolites for Hypertensive Emergencies: Effect on Hemodynamics and Cardiac Conductance. *Frontiers in Pharmacology*, 12 (June), 1-10. doi.org/10.3389/fphar.2021.681070

Afroz, A., Haque, T., Talukder, M. U., & Islam, S. A. (2011). Spectrophotometric Estimation of Rosuvastatin Calcium and Glimepiride in Tablet Dosage Form. *Asian J. Pharm.*, 1(4), 74-78.

Aguilar-de-Leyva, Á., Linares, V., Casas, M., & Caraballo, I. (2020). 3D Printed Drug Delivery Systems Based on Natural Products. *Pharmaceutics*, 12(7), 620. doi.org/10.3390/pharmaceutics12070620

Ahmed, O. A. A., Badr-Eldin, S. M., Tawfik, M. K., Ahmed, T. A., El-Say, K. M., & Badr, J. M. (2014). Design and optimization of self-nanoemulsifying delivery system to enhance quercetin hepatoprotective activity in paracetamol-induced hepatotoxicity. *Journal of Pharmaceutical Sciences*, 103(2), 602-612. doi.org/10.1002/jps.23834

Aimar, A., Palermo, A., & Innocenti, B. (2019). The Role of 3D Printing in Medical Applications: A State of the Art. *Journal of Healthcare Engineering*, 2019. doi.org/10.1155/2019/5340616

Arshami, J., Pilevar, M., Aami Azghadi, M., & Raji, A. R. (2013). Hypolipidemic and antioxidative effects of curcumin on blood parameters, humoral immunity, and jejunum histology in Hy-line hens. *Avicenna Journal of Phytomedicine*, 3(2), 178-185. doi.org/10.22038/ajp.2013.72

Battle, A., Mostafavi, S., Zhu, X., Potash, J. B., Weissman, M. M., McCormick, C., Haudenschild, C. D., Beckman, K. B., Shi, J., Mei, R., Urban, A. E., Montgomery, S. B., Levinson, D. F., & Koller, D. (2014). Characterizing the genetic basis of transcriptome diversity through RNA-sequencing of 922 individuals. *Genome Research*, 24(1), 14-24. doi.org/10.1101/gr.155192.113

Cenik, C., Cenik, E. S., Byeon, G. W., Grubert, F., Candille, S. I., Spacek, D., Alsallakh, B., Tilgner, H., Araya, C. L., Tang, H., Ricci, E., & Snyder, M. P. (2015). Integrative analysis of RNA, translation, and protein levels reveals distinct regulatory variation across humans. *Genome Research*, 25(11), 1610-1621. doi.org/10.1101/gr.193342.115

El-Say, K. M., Ahmed, T. A., Badr-Eldin, S. M., Fahmy, U., Hibah, A., & Ahmed, O. A. A. (2015). Enhanced permeation parameters of optimized nanostructured simvastatin transdermal films: ex vivo and in vivo evaluation. *Pharmaceutical Development and Technology*, 20(8), 919-926. doi.org/10.3109/10837450.2014.938859

Haines, J. L., Hauser, M. A., Schmidt, S., Scott, W. K., Olson, L. M., Gallins, P., Spencer, K. L., Shu, Y. K., Noureddine, M., Gilbert, J. R., Schnetz-Boutaud, N., Agarwal, A., Postel, E. A., & Pericak-Vance, M. A. (2005). Complement factor H variant increases the risk of age-related macular degeneration. *Science,* 308(5720), 419-421. doi.org/10.1126/science.1110359

Jamróz, W., Szafraniec, J., Kurek, M., & Jachowicz, R. (2018). 3D printing in pharmaceutical and medical applications. *Pharmaceutical Research,* 35(9), Article 176.

Katstra, W. E., Palazzolo, R. D., Rowe, C. W., Giritlioglu, B., Teung, P., & Cima, M. J. (2000). Oral dosage forms fabricated by Three Dimensional Printing™. *Journal of Controlled Release,* 66(1), 1-9. doi.org/10.1016/S0168-3659(99)00225-4

Khaled, S. A., Burley, J. C., Alexander, M. R., Yang, J., & Roberts, C. J. (2015). 3D printing of tablets containing multiple drugs with defined release profiles. *International Journal of Pharmaceutics,* 494(2), 643-650. doi.org/10.1016/j.ijpharm.2015.07.067

Kim, M., & Kim, Y. (2010). Hypocholesterolemic effects of curcumin via up-regulation of cholesterol 7a-hydroxylase in rats fed a high fat diet. *Nutrition Research and Practice,* 4(3), 191. doi.org/10.4162/nrp.2010.4.3.191

Lesko, L. J. (2007). Personalized medicine: Elusive dream or imminent reality? In *Clinical Pharmacology and Therapeutics* (Vol. 81, Issue 6, pp. 807-816). Clin Pharmacol Ther. doi.org/10.1038/sj.clpt.6100204

Liju, V. B., Jeena, K., & Kuttan, R. (2011). An evaluation of antioxidant, anti-inflammatory, and antinociceptive activities of essential oil from *Curcuma longa.* L. *Indian Journal of Pharmacology,* 43(5), 526-531. doi.org/10.4103/0253-7613.84961

Lu, Y., Goldstein, D. B., Angrist, M., & Cavalleri, G. (2014). Personalized Medicine and Human Genetic Diversity. *Cold Spring Harb Perspect Med.,* 4(9), 1-11.

Nabavi, S., Thiagarajan, R., Rastrelli, L., Daglia, M., Sobarzo-Sanchez, E., Alinezhad, H., & Nabavi, S. (2015). Curcumin: A Natural Product for Diabetes and its Complications. *Current Topics in Medicinal Chemistry,* 15(23), 2445-2455. doi.org/10.2174/1568026615666150619142519

Oliveira, S., Monteiro-Alfredo, T., Silva, S., & Matafome, P. (2020). Curcumin derivatives for Type 2 Diabetes management and prevention of complications. In *Archives of Pharmacal Research* (Vol. 43, Issue 6, pp. 567-581). Pharmaceutical Society of Korea. doi.org/10.1007/s12272-020-01240-3

Parsamanesh, N., Moossavi, M., Bahrami, A., Butler, A. E., & Sahebkar, A. (2018). Therapeutic potential of curcumin in diabetic complications. In *Pharmacological Research* (Vol. 136, pp. 181-193). Academic Press. doi.org/10.1016/j.phrs.2018.09.012

Rahman, L., Rowe, P., Cheyne, A., & Wilson, D. I. (2002). Ram extrusion of potato starch dough through multi-holed dies. *Food and Bioproducts Processing: Transactions of the Institution of Chemical Engineers, Part C,* 80(1), 12-19. doi.org/10.1205/096030802753479061

Roy, A., Roy, K., Roy, S., Deb, J., Ghosh, A., & Ali, K. A. (2012). Response surface optimization of sustained release metformin-hydrochloride matrix tablets: influence of some hydrophillic polymers on the release. *ISRN Pharmaceutics,* 2012, 364261. doi.org/10.5402/2012/364261

USP 41-NF 36. (2018). *The united States Pharmacopeia National Formulary.* Twinbrook Parkway, Rockville, Md.: The United States Pharmacopeial Convention.

Vogenberg, F. R., Barash, C. I., & Pursel, M. (2010). Personalized medicine—Part 1: Evolution and development into theranostics. In *P and T* (Vol. 35, Issue 10, p. 560). MediMedia, USA. /pmc/articles/PMC2957753/

Wu, L., Candille, S. I., Choi, Y., Xie, D., Jiang, L., Li-Pook-Than, J., Tang, H., & Snyder, M. (2013). Variation and genetic control of protein abundance in humans. *Nature,* 499(7456), 79-82. doi.org/10.1038/nature12223

Zhang, M., Rough, S. L., Ward, R., Seiler, C., & Wilson, D. I. (2011). A comparison of ram extrusion by single-holed and multi-holed dies for extrusion-spheronisation of microcrystalline-based pastes. *International Journal of Pharmaceutics,* 416(1), 210-222. doi.org/10.1016/j.ijpharm.2011.06.043

Zidan, A., Alayoubi, A., Coburn, J., Asfari, S., Ghammraoui, B., Cruz, C. N., & Ashraf, M. (2019). Extrudability analysis of drug loaded pastes for 3D printing of modified release tablets. *International Journal of Pharmaceutics,* 554 (September 2018), 292-301. doi.org/10.1016/j.ijpharm.2018.11.025

Zilcha-Mano, S. (2020). Toward Personalized Psychotherapy: The Importance of the Trait-Like/State-Like Distinction for Understanding Therapeutic Change. *American Psychologist.* doi.org/10.1037/amp0000629

Example 4

Preparation and Characterization of Curcuma Oil-Based SNEDDS

An optimized Curcuma oil-based self-nanoemulsifying drug delivery system (SNEDDS) formulation was prepared in a screw cap vial by accurately weighing the specified amount of *Curcuma longa* oil (15%), Tween 80 (10%), and PEG 400 (75%). The formulation components were vortex for 60 s to get a homogenous dispersion.

To evaluate the size and polydispersity index (PDI) of the prepared formulation, 1 g of the prepared SNEDDS was added to 10 mL of distilled water on a magnetic stirrer until a homogenous yellowish nanoemulsion was obtained. The size and PDI of the obtained emulsion were analyzed using Malvern Zetasizer Nano ZSP, Malvern Panalytical Ltd. (Malvern, UK).

Preparation and In Vitro Characterization of 3D-Printed Polypills

To develop medicated 3D-printed polypills, hydroxypropyl methylcellulose gel pastes were first prepared. SNEDDS-based gel pastes and non-SNEDDS gel pastes loaded with either GMD or RSV were prepared. Non-SNEDDS gel pastes were prepared by dispersing the known weight of GMD or RSV to a specified volume of distilled water over a magnetic stirrer and 4% of HPMC was added. Stirring was continued until homogenous gels were obtained that were kept in the refrigerator for 24 h at 4° C. for complete swelling of the polymer. Gels containing the optimized SNEDDS formulation were prepared by dispersing the specified weight of GMD or RSV in 2 g of SNEDDS and adding the medicated SNEDDS to 18 mL of distilled water on a magnetic stirrer. Finally, HPMC (4%) was added with continuous stirring and the mixtures were left in the refrigerator. Plain (drug-free) SNEDDS-based gel formulation was also prepared with the same procedure to be used as a control in the assessment of pharmacodynamic activity.

Different tablet excipients were added to the prepared gels to develop pastes suitable for tablet printing. Avicel (20% w/w) as an insoluble ingredient, lactose (10% w/w) and Methocel (5% w/w) as adsorbent for the SNEDDS formulation, PVP K90 (10% w/w) as a binder, and Ac-Di-Sol (5% w/w) as a disintegrant was gradually mixed to the prepared gels in a mortar until a homogenous paste was obtained. Five different paste formulations were prepared namely, plain (non-medicated) SNEDDS-loaded paste, non-SNEDDS-loaded GMD paste, non-SNEDDS-loaded RSV paste, SNEDDS-loaded GMD paste, and SNEDDS-loaded RSV paste. The flow properties and viscosity values of the prepared pastes were studied using a Kinexus oscillation rheometer (Malvern Instruments Ltd. Worchestershire, UK).

Three-dimensional printed (3D-P) pills were developed from the prepared pastes utilizing REGEMAT3D V1 Bio-Printer (REGEMAT Inc. Granada, Spain). A computer-aided design modeling software (REGEMAT 1.4.9 Designer) was used during the printing process. Each paste formulation was loaded into the extrusion tool and extruded through a 0.58 mm printing nozzle. The flow speed was adjusted at 2.6 mm/s and the infill speed was 10 mm/s. Printing was done layer-by-layer in a horizontal and vertical direction at room temperature. For each formulation, a total of eight layers were printed in the selected area of the building plate to develop a cylinder of 15 mm diameter. The printing process was conducted for the prepared five gel paste formulations. Another multi-compartment tablet (polypill) formulation was printed utilizing eight layers of the paste containing GMD and eight layers of the paste containing RSV. All the printed tablet formulations were dried in a vacuum dryer at 40° C. for 24 hours and finally kept in a hermetically sealed container. The quality attributes of the prepared tablets were evaluated according to the specification stated in the United States Pharmacopeia [1].

Example 5

In Vivo Studies on the Induced Hyperglycemic/Hyperlipidemic Rats
Study Design, Animal Handling and Pharmacokinetics Evaluation A single dose one-period parallel design was used to study the pharmacokinetics of GMD and RSV from the prepared 3D-P polypills (F2-F6). Male Wistar rats of an average weight of 200-250 g were used. Normal animals without treatment were used as a control. Diabetes was induced in the studied animals by intraperitoneal injection of 50 mg/kg streptozotocin two weeks before the study. Fasting blood glucose level was assessed using All Medicus GlucoDr SuperSensor Device (AGM-2200), All Medicus Co. Ltd., (Gyeonggi-do, REPUBLIC of KOREA). Rats having moderate diabetes, with fasting blood glucose levels in the range of 200-300 mg/100 ml, were selected. Hyperlipidemia was induced in animals by intraperitoneal injection of 0.25 g/kg Poloxamer 407 dissolved in 0.9% saline, 24 h before drug administration. Animals with hyperlipidemia and hyperglycemia were classified into six groups (6 per each). Group, I was assigned as a control group while group II was assigned for animals with induced hyperlipidemia and hyperglycemia without treatment (model group). Group III, IV, V, VI, and VII were administered tablet formulations F1, F2, F3, F4, and F5. Before animal treatment, rats were kept in a temperature-controlled closed area with a 12-h light/darkness cycle for one week with free access to water and food. GMD and RSV doses of 10 mg/kg and 20 mg/kg, respectively were used [2,3]. Each 3D-P tablet formulation was crushed and suspended in 1% carboxymethyl cellulose to prepare an oral drug suspension suitable for administration through a gastric tube. Blood samples were collected from all animals through retro-orbital puncturing. Withdrawal of the blood samples was conducted over 24 h for animals treated with GMD. The blood sampling was extended to 72 h for groups administered RSV. The plasma was immediately separated from the blood samples by centrifugation at 6,000 rpm for 10 min and stored frozen at −20° C. until analysis. Blank plasma samples were collected from the studied animals before treatment to construct a calibration standard. The protocol for this study received approval from the Research Ethics Committee, Faculty of Pharmacy, King Abdulaziz University, KSA (Reference No. 1021442). The study was conducted according to the guidelines of Good Clinical Practice, the International Conference on Harmonization, and the European Medicines Agency.

Chromatographic Conditions

Calibration curves for GMD and RSV were constructed from blank rat plasma samples. For the determination of GMD, calibration standards were prepared from drug and metformin (internal standard) methanolic stock solutions. The plasma GMD concentration in the unknown and the prepared calibration standards was determined using Perkin Elmer high-performance liquid chromatography (HPLC) equipped with variable wavelength UV detector and autosampler. Phenomenex, RP Hi-Q-Sil C18 column (250× 4.6 mm, 5 µm, Phenomenex Inc.) was used for separation. The mobile phase consisted of (64:36) acetonitrile and potassium dihydrogen orthophosphate (0.02 M) adjusted to pH 3.5. The injection volume used was 30 µL. The flow rate of the mobile phase was adjusted at 1 mL/min. The UV detector was adjusted at 230 nm. For extraction and preparation of the samples; 1 mL of acetonitrile-methanol (1:1) mixture was added to each sample. The mixture was vortexed for 1 minute and centrifuged for 10 minutes at 5000 rpm. The organic phase was separated and evaporated to dryness under a constant stream of nitrogen at 50° C. The residue was reconstituted in 80 µL of the mobile phase and a volume of 30 µL was injected. The condition employed for quantification of GMD in the plasma samples was conducted as previously mentioned except for a slight modification [4].

For RSV determination, atorvastatin was used as an internal standard. Quantification of RSV in the calibration standards and the unknown samples was performed using the same apparatus and condition mentioned above for GMD except that the mobile phase consisted of acetonitrile and 0.1% phosphoric acid (58:42) and the UV detector was adjusted at 240 nm. Extraction and separation of RSV were achieved as described above for GMD except that the residue was reconstituted in 80 µl of acetonitrile and 0.1% phosphoric acid (58:42). The analysis of RSV in the plasma samples was performed under the same condition as previously reported [3]. PK solver (An add-in program for pharmacokinetic data) was utilized to calculate the pharmacokinetic parameters using the non-compartmental extravascular pharmacokinetic model. Maximum plasma drug concentration ($C_{max}$), time to reach the maximum plasma drug concentration ($T_{max}$), the area under the plasma drug concentration-time curve to the last time point ($AUC_{0-t}$) and to infinity ($AUC_{0-inf}$), the area under the moment of the plasma drug concentration-time curve from time zero to infinity ($AUMC_{0-inf}$), the elimination rate constant (Lambda_z), the mean residence time (MRT), elimination half-life ($t_{1/2}$), total body clearance (Cl/F) and the apparent volume of distribution (vz/F) were measured.

Pharmacodynamics Study (Hypoglycemic and Hypolipidemic Effects)

The blood glucose level (BGL) in the studied animals was measured 24 h after the administration of a single oral dose of 10 mg/kg GMD formulations by intragastric tubing. Blood samples were collected through retro-orbital puncturing from groups of animals administered GMD formulations for a comparison with the group of animals that received the plain Curcuma oil-loaded SNEDDS over 24 h.

The hypolipidemic activity was evaluated in the groups of animals that were administered with RSV formulations and compared with the group of animals that received the plain Curcuma oil-loaded SNEDDS over 72 h. Serum was separated by keeping the collected blood samples for 1 h in the centrifuge tubes to allow clotting, followed by a centrifugation for 15 minutes at 3000 rpm. The separated serum samples were assessed for total cholesterol, triglycerides (TG), low-density lipoproteins (LDL), and high-density lipoproteins (HDL) using (Colorimetric/Fluorometric) Assay Kit (ab65390), which provides a simple quantification method of the studied parameters after convenient separation of the different lipoprotein fractions.

Hepatoprotective and Antioxidant Activities

The liver function of the studied animals was evaluated before and after treatment by assessing the serum levels of aspartate aminotransferase (AST), alanine aminotransferase (ALT), and alkaline phosphatase (ALP) enzymes. The concentrations of these enzymes were measured using the colorimetric method utilizing Spectrum diagnostic ALT, AST, and ALP reagents of the Egyptian company for biotechnology (Cairo, Egypt). The reagents were supplied in the ready-to-use kit and they are used only with non-haemolyzed serum samples. Heparin and EDTA are the only acceptable anticoagulants. Measurement was performed at 546 nm at a sample with a reagent ratio of 1:60.

Also, the antioxidant activity was measured by monitoring the serum levels of catalase (CAT), glutathione transferase (GST), and superoxide dismutase (SOD) enzymes. CAT and SOD serum concentrations were measured using colorimetric assay kits of Bio-diagnostic (Giza, Egypt), catalog #CA 25 17 and SD 25 21 for CAT and SOD, respectively. GST was quantified using rat Glutathione S-transferase (GSTs) ELISA Kit (Catalog #MBS260372).

Histopathological Examination of Liver and Pancreas Tissues

The animals under the study were sacrificed, and the liver and pancreas specimens were taken and treated with 10% neutral buffer formalin. Paraffin sections were prepared at the desired thickness using a microtome and stained with hematoxylin and eosin. Finally, any changes in the tissues of the pancreas and liver were microscopically investigated [5]. Histopathological lesion of the liver samples was examined for steatosis following the criteria of Brunt et al [6]. Briefly, macro-vesicular steatosis was graded 0-3 based on the percent of hepatocytes in the biopsy (0 is none; 1 is up to 33%; 2 is 33-66%; 3 is >66%), zonal distribution of steatosis and the presence of microvesicular steatosis were noted. Also, the area of islets of Langerhans was microscopically examined in the pancreas specimens of the investigated groups to evaluate the protective and/or therapeutic effect of 3D-P polypills in the pancreas tissue.

Statistical Analysis

The obtained data for the pharmacokinetics of GMD and RSV were expressed as mean±SD and statistically analyzed utilizing the GraphPad Prism 8 software (GraphPad Inc., La Jolla, Calif., USA). Regarding the plasma concentration-time curve, two-way ANOVA followed by Tukey's multiple comparisons test was done to compare each means with the other at all time points to assess the significance between groups. The biochemical parameters were also assessed for their statistical difference using the two-way ANOVA followed by Tukey's multiple comparisons test, as well as a two-tailed unpaired t-test was used to assess the difference between the biochemical parameters of the normal and model groups. Results with $P<0.05$ were considered significant.

Example 6

Development of SNEDDS

In some embodiments, curcuma oil was used to develop SNEDDS with Tween 80 as a surfactant and PEG 400 as a cosurfactant. An optimized SNEDDS formulation that contains 15%, 10%, and 75% of Curcuma oil, surfactant, and cosurfactant, respectively was prepared and characterized for droplet size. The observed value for the particle size and PDI were found to be 94.43 nm and 0.544, respectively.

Preparation and Characterization of 3D Printed Polypills

All the prepared pastes exhibited a shear-thinning behavior of a pseudoplastic flow type. The obtained values for the viscosity of the studied pastes were 6550±278, 8604±295, 9185±153, 6648±135 and 6684±451 Pa·s. The presence of the Curcuma oil-based SNEDDS in formulations leads to lower viscosity values due to lubrication of the solid particles and prevention of water loss from the paste. The obtained dried pills were cylindrical in shape and exhibited a weight of 532.58±23.7, 90.53±27.76, 498.88±55.32, 541.68±61.02, 559.39±41.45 and 1067.54±77.32 mg; a thickness of 3.035±0.038, 2.647±0.160, 2.826±0.228, 3.239±0.178, 2.876±0.128 and 5.797±0.156 mm; a diameter of 14.656±0.148, 13.289±0.485, 15.201±0.228, 14.855±0.319, 14.082±0.249 and 14.342±0.109 mm. GMD containing pills demonstrated a drug content of 3.98±0.201, 3.918±0.219 and 4.052±0.087 mg while RSV containing pills illustrated a drug content of 9.76±0.359, 9.691±0.594, and 9.711±0.097 mg. Good mechanical strength was obtained for all the prepared pills as indicated from the friability value which was less than 1%. Throughout the disclosure, the term "3D-printed tablets" and "3D-printed polypills" are used interchangeably.

Assessment of Pharmacokinetic Parameters

Figure 6A:
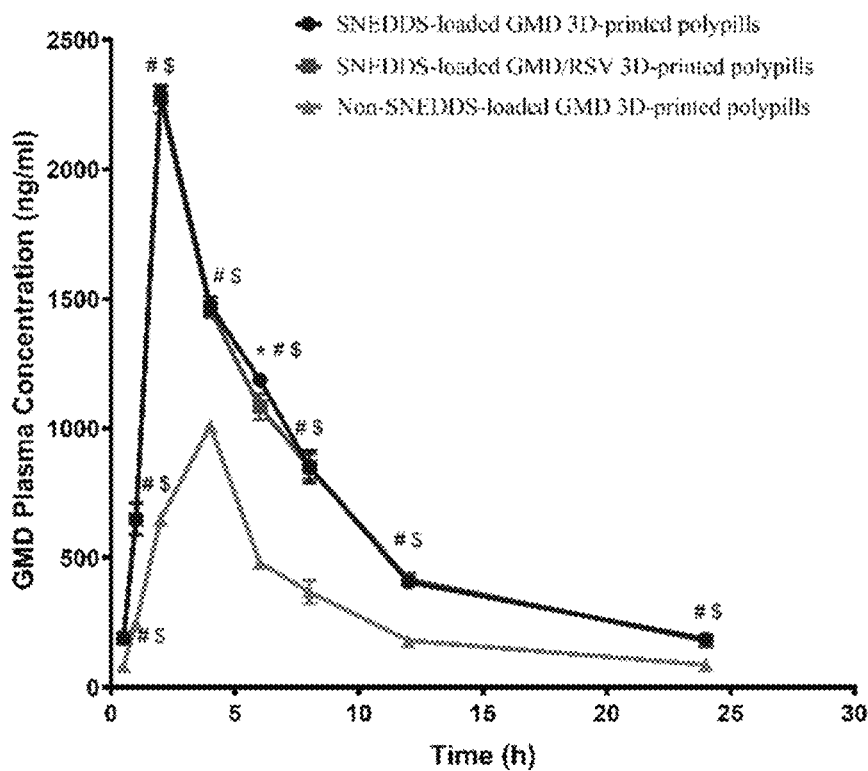
FIGS. 6A-B show plasma concentration-time curves for (A) GMD and (B) RSV after oral administration of the 3D-printed tablets to induced-hyperglycemic/hyperlipidemic male Wistar rats. Significant difference was considered at $P<0.05$. Data are presented as mean±SD, (n=6).

FIG. 6A depicts the plasma concentration-time profiles for the SNEDDS-loaded GMD pills and SNEDDS-loaded GMD/RSV pills in comparison to non-SNEDDS-loaded GMD pills after a single oral administration of 10 mg/kg of body weight for the induced-hyperglycemic/hyperlipidemic male Wistar rats. The figure and the two-way ANOVA showed the significant difference (p-value <0.05) between the SNEDDS-loaded pills and the non-SNEDDS-loaded ones at all the time points of the study. The calculated values of the pharmacokinetic parameters for GMD from all formulations are summarized in Table 1. The results revealed that the loading of GMD in the Curcuma oil-based SNEDDS hasten the absorption of the drug to reach its maximum plasma concentration ($C_{max}$) after 2 h instead of 4 h in the case of non-SNEDDS-loaded 3D-P pills. Compared with non-SNEDDS-loaded 3D-P pills, the $C_{max}$ of GMD for SNEDDS-loaded GMD 3D-P pills and SNEDDS-loaded GMD/RSV 3D-P polypills were improved by more than 2 times. Also, SNEDDS-loaded GMD 3D-P pills and SNEDDS-loaded GMD/RSV 3D-P polypills showed a significantly higher area under the curve (16,263.25±459.36 and 16,035.25±371.43 ng/mL×h), respectively, in comparison to the non-SNEDDS-loaded 3D-P pills (7,245.83±386.63 ng/mL×h), which reflected on the significant increase in the relative bioavailability with 219.75% and 217.16%, respectively.

TABLE 1

Pharmacokinetic parameters of GMD after oral administration of 10 mg/kg in rats (n = 6, the data expressed as mean ± SD)

| Parameter | Unit | Non-SNEDDS-loaded GMD pills | SNEDDS-loaded GMD pills | SNEDDS-loaded GMD/RSV pills |
|---|---|---|---|---|
| Lambda_z | 1/h | 0.09 (±0.00) | 0.11 (±0.01) | 0.10 (±0.00) |
| $t_{1/2}$ | h | 7.49$^{a,b}$ (±0.18) | 6.36 (±0.41) | 6.68 (±0.14) |
| $T_{max}$ | h | 4.00$^{a,b}$ (±0.00) | 2.00 (±0.00) | 2.00 (±0.00) |
| $C_{max}$ | ng/ml | 1,008.67$^{a,b}$ (±23.29) | 2,290.33 (±31.39) | 2,270.00 (±52.43) |
| $AUC_{0-t}$ | ng/ml * h | 7,245.83$^{a,b}$ (±386.63) | 16,263.25 (±459.36) | 16,035.25 (±371.43) |
| $AUC_{0-inf}$ | ng/ml * h | 8,178.36$^{a,b}$ (±419.23) | 17,971.77 (±562.95) | 17,759.83 (±337.25) |
| $AUMC_{0-inf}$ | ng/ml * h^2 | 87,046.63$^{a,b}$ (±5,116.42) | 176,440.39 (±10,605.80) | 176,286.42 (±1,884.49) |
| $MRT_{0-inf}$ | h | 10.64 (±0.21) | 9.81 (±0.35) | 9.93 (±0.17) |
| Vz/F | (mg)/(ng/ml) | 0.01 (±0.00) | 0.01 (±0.00) | 0.01 (±0.00) |
| Cl/F | (mg)/(ng/ml)/h | 0.00 (±0.00) | 0.00 (±0.00) | 0.00 (±0.00) |
| F | % | — | 219.75 | 217.16 |

$^a$Significantly different from values of SNEDDS-loaded GMD pills with p-value <0.05.
$^b$Significantly different from values of SNEDDS-loaded GMD/RSV pills with p-value <0.05.

TABLE 2

Pharmacokinetic parameters of RSV after oral administration of 20 mg/kg in rats (n = 6, the data expressed as mean ± SD)

| Parameter | Unit | Non-SNEDDS-loaded RSV pills | SNEDDS-loaded RSV pills | SNEDDS-loaded GMD/RSV pills |
|---|---|---|---|---|
| Lambda_z | 1/h | 0.03 (±0.00) | 0.03 (±0.00) | 0.03 (±0.00) |
| $t_{1/2}$ | h | 23.20 (±0.28) | 23.02 (±0.22) | 22.79 (±0.15) |
| $T_{max}$ | h | 4.00$^{a,b}$ (±0.00) | 2.00 (±0.00) | 2.00 (±0.00) |
| $C_{max}$ | ng/ml | 901.00$^{a,b}$ (±10.00) | 2,062.00 (±38.30) | 2,036.67 (±22.50) |
| $AUC_{0-t}$ | ng/ml * h | 30,085.67$^{a,b}$ (±645.03) | 68,414.25 (±1,461.16) | 67,811.75 (±1,470.46) |
| $AUC_{0-inf}$ | ng/ml * h | 34,101.93$^{a,b}$ (±783.83) | 77,371.16 (±1,811.78) | 76,482.63 (±1,678.71) |
| $AUMC_{0-inf}$ | ng/ml * h^2 | 1,175,344.38$^{a,b}$ (±36,253.05) | 2,652,298.87 (±84,867.52) | 2,600,769.10 (±70,329.74) |
| $MRT_{0-inf}$ | h | 34.46 (±0.31) | 34.28 (±0.30) | 34.00 (±0.18) |
| Vz/F | (mg)/(ng/ml) | 0.02 (±0.00) | 0.01 (±0.00) | 0.01 (±0.00) |
| Cl/F | (mg)/(ng/ml)/h | 0.00 (±0.00) | 0.00 (±0.00) | 0.00 (±0.00) |
| F | % | — | 229.88 | 224.28 |

$^a$Significantly different from values of SNEDDS-loaded RSV pills with p-value <0.05.
$^b$Significantly different from values of SNEDDS-loaded GMD/RSV pills with p-value <0.05.

Figure 6B:
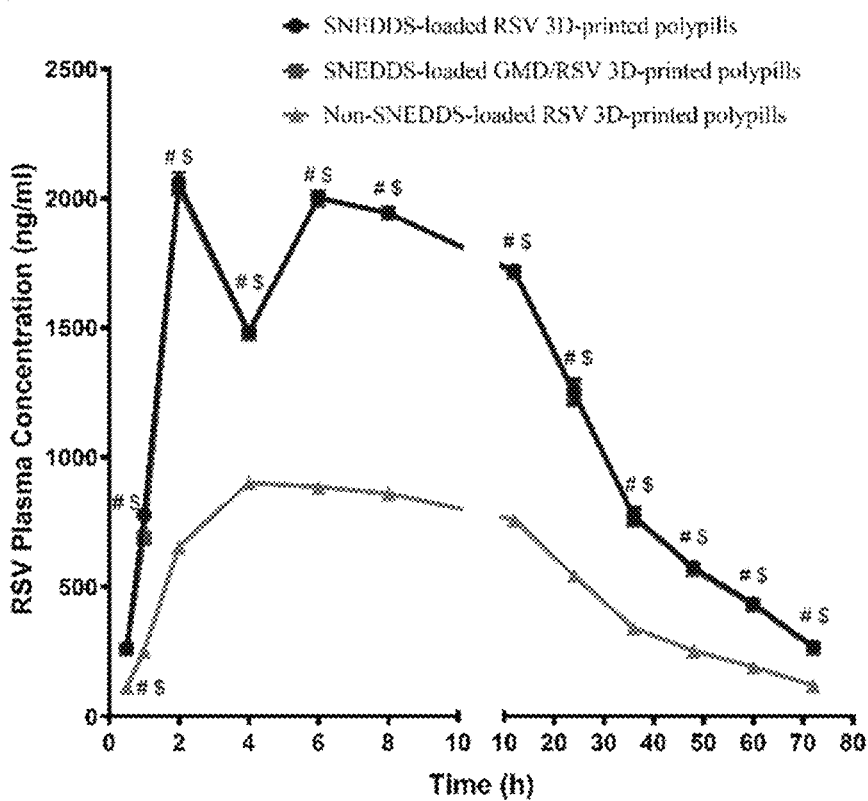

The same behavior was achieved in the plasma concentration-time profiles for the SNEDDS-loaded RSV pills and SNEDDS-loaded GMD/RSV pills in comparison to non-SNEDDS-loaded RSV pills after a single oral administration of 20 mg/kg of body weight for the induced-hyperglycemic/hyperlipidemic male Wistar rats as depicted in FIG. 6B. The plasma concentrations of RSV of SNEDDS-loaded RSV pills and SNEDDS-loaded GMD/RSV pills were significantly (p-value <0.05) higher than those of non-SNEDDS-loaded RSV pills at all time points of the study. The calculated values of the pharmacokinetic parameters for RSV from all formulations are summarized in Table 2. The $t_{max}$ was 2 h in the SNEDDS-loaded RSV 3D-P pills instead of 4 h in the case of non-SNEDDS-loaded 3D-P pills. Also, the value of $C_{max}$ for the SNEDDS-loaded RSV 3D-P pills and SNEDDS-loaded GMD/RSV 3D-P polypills were 2,062.00±38.30 ng/ml and 2,036.67±22.50 ng/ml, respectively, versus 901.00±10.00 ng/ml for non-SNEDDS-loaded 3D-P pills. Also, SNEDDS-loaded RSV 3D-P pills and SNEDDS-loaded GMD/RSV 3D-P polypills showed significantly higher area under the curve ($AUC_{0-t}$) of 68,414.25±1,461.16 and 67,811.75±1,470.46 ng/ml×h, respectively, in comparison to the non-SNEDDS-loaded 3D-P pills (30,085.67±645.03 ng/ml×h). These findings reflected the significant increase in the relative bioavailability of RSV from the SNEDDS-loaded RSV 3D-P pills and SNEDDS-loaded GMD/RSV 3D-P polypills were 219.75% and 217.16%, respectively compared with that of non-SNEDDS-loaded 3D-P pills.

The plasma concentration-time profile following a single oral dose of SNEDDS-loaded RSV showed two separate peaks (i.e.g, the first peak at 2 h and the second peak at 6 h), which is known as the Double Peak Phenomenon. This phenomenon is explained by either enterohepatic recirculation, delayed gastric emptying, and/or variability of absorption [13]. In enterohepatic recirculation, the first peak in the profile is often the largest of the two peaks which were observed in our case with RSV loaded-SNEDDS. This phenomenon is attributed to the circulation of bile from the liver to the small intestine, where it promotes the digestion of fats and other substances and back to the liver, which is in full agreement with the reported enhanced bioavailability of silymarin SMEDDS [14]. Also, the absence of the double peaks after oral administration of non-SNEDDS-loaded RSV formulation may be useful to negate the variability of absorption or the presence of two absorption sites along the gastrointestinal tract [15].

The obtained results suggest that the incorporation of GMD and RSV in Curcuma oil-based SNEDDS with minimum globule size, loading onto 3D-P pills lead to an increase in the rate and extent of absorption as well as improving the oral bioavailability of these drugs which is in agreement with the previously reported results [3,5,16-18]. This improvement will be assessed and confirmed by the biochemical analysis of blood glucose level, TC, TG, HDL, and LDL as well as the calculation of the atherosclerotic index (AI), as a marker of cardiovascular disease.

Assessment of Hypoglycemic Efficacy

Figure 7A:
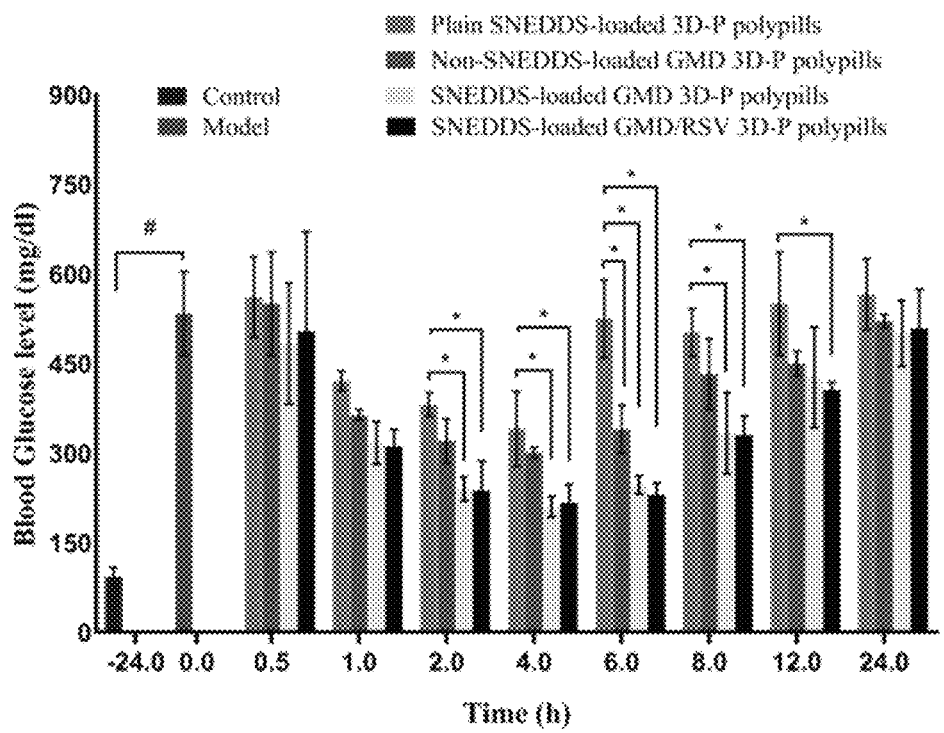
FIGS. 7A-B show (A) blood glucose level and (B) the percentage of inhibition of blood glucose level after oral administration of the 3D-printed tablets to induced-hyperglycemic/hyperlipidemic male Wistar rats. Significant difference was considered at $P<0.05$. Data are presented as mean±SD, (n=3).
Figure 7B:
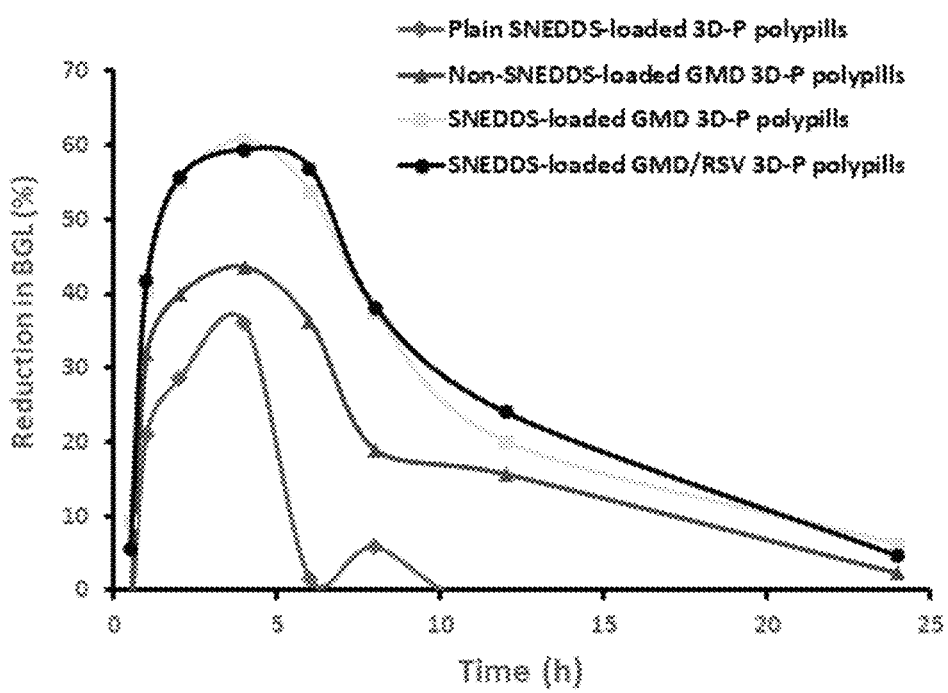

A significant increase (p<0.05) in BGL in the induced-hyperglycemic rats (model) was observed when compared with that of the normal rats (control) as depicted in FIG. 7A. This finding confirms the induction of diabetes in the rats after intraperitoneal injection of 50 mg/kg streptozotocin two weeks before the study. It is noticed that the plain SNEDDS-loaded pills containing only Curcuma oil showed a slight reduction in BGL over 4 h compared with the model group. Also, a significant reduction in BGL was noticed after administration of non-SNEDDS-loaded GMD pills that extended only for 6 h and then substantially increased. The hypoglycemic efficacy of SNEDDS-loaded GMD pills and SNEDDS-loaded GMD/RSV pills have shown a significant reduction (p<0.05) after 1 h and extended to 8 h after administration. This significant reduction appeared in comparison with the model group and plain SNEDDS-loaded pills. On the other hand, there is no significant difference between SNEDDS-loaded GMD pills and SNEDDS-loaded GMD/RSV pills. FIG. 7B revealed a percentage reduction of BGL after administration of a single dose of SNEDDS-loaded GMD pills or SNEDDS-loaded GMD/RSV pills of ~40% after 1 h and ~60% after 4 h and this reduction was extended for 8 h with ~40% from the model group. On the other hand, non-SNEDDS-loaded GMD pills showed a percentage reduction in BGL from 30 to 40% for not more than 6 h. This indicates that the duration of action of the SNEDDS-loaded formulations is markedly longer than that of the non-SNEDDS-loaded formulations.

Assessment of Hypolipidemic Efficacy

Figure 8A:
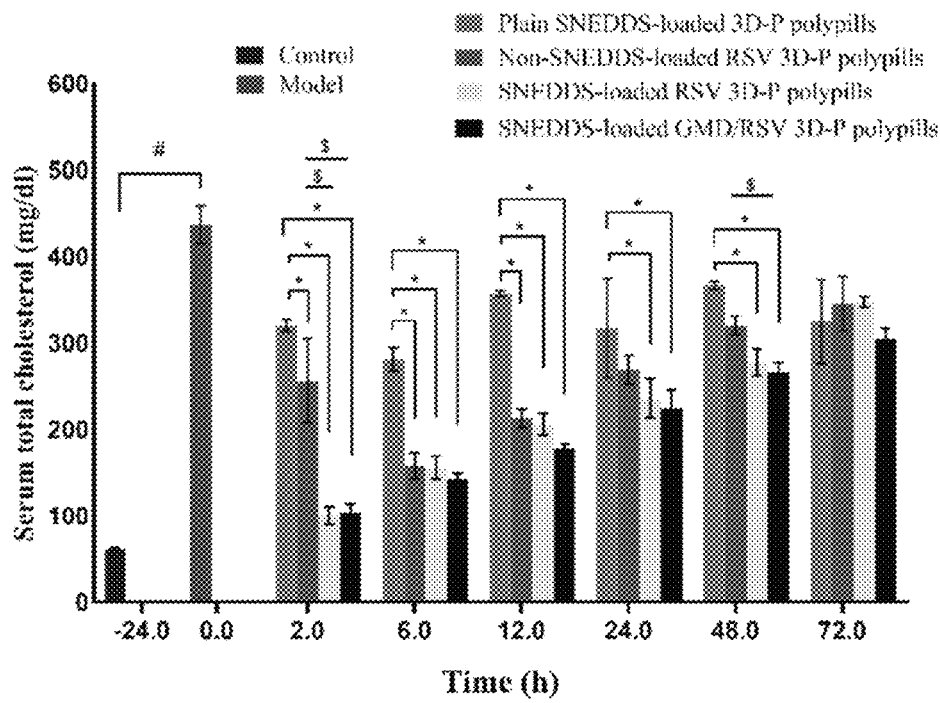
FIGS. 8A-D show serum lipid profile in induced-hyperglycemic/hyperlipidemic male Wistar rats after oral treatment with a single dose of the prepared 3D-printed polypills. (A) levels of total cholesterol; (B) levels of triglycerides; (C) LDL levels and (D) HDL levels. (#) indicates significant from the control group. (*) indicates significant from plain SNEDDS-loaded 3D-P pills. ($) indicates significant from non-SNEDDS-loaded 3D-P pills. Significant difference was considered at $P<0.05$. Data are presented as mean±SD, (n=3).
Figure 8B:
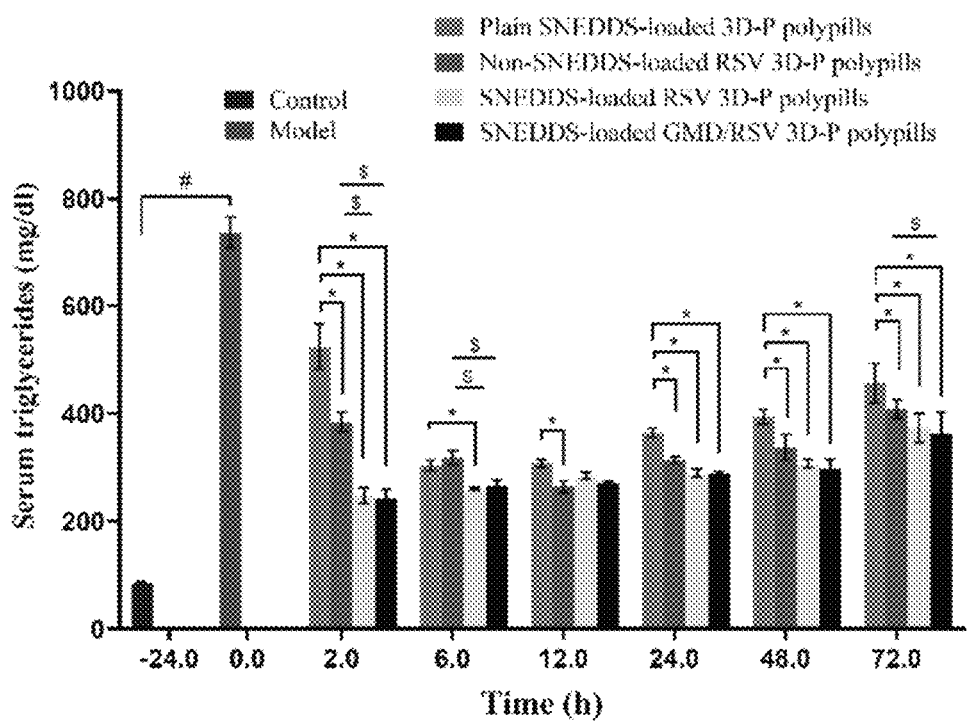
Figure 8C:
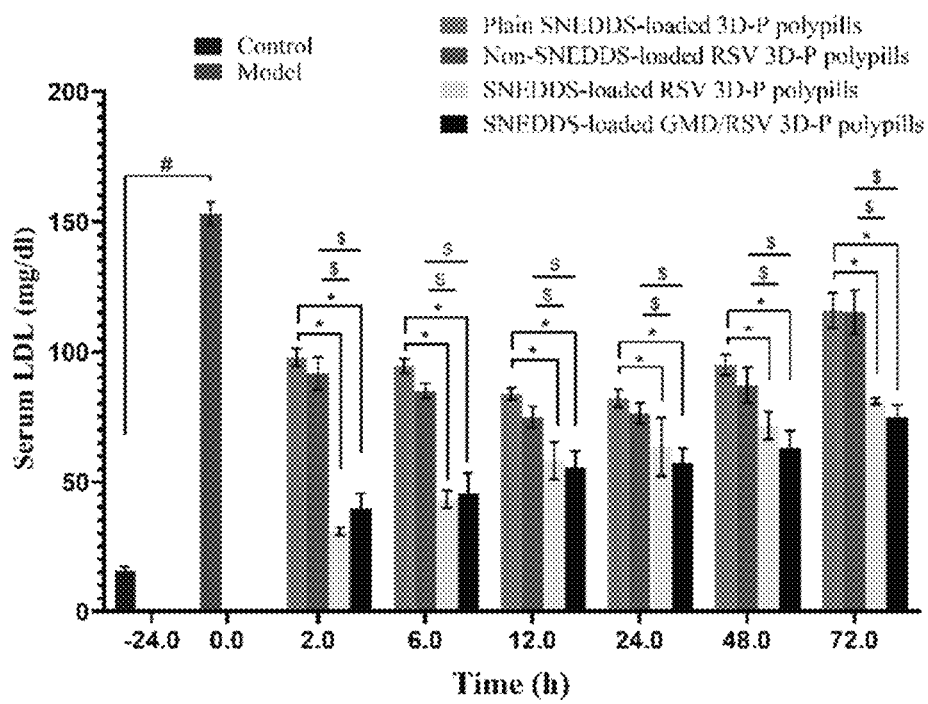
Figure 8D:
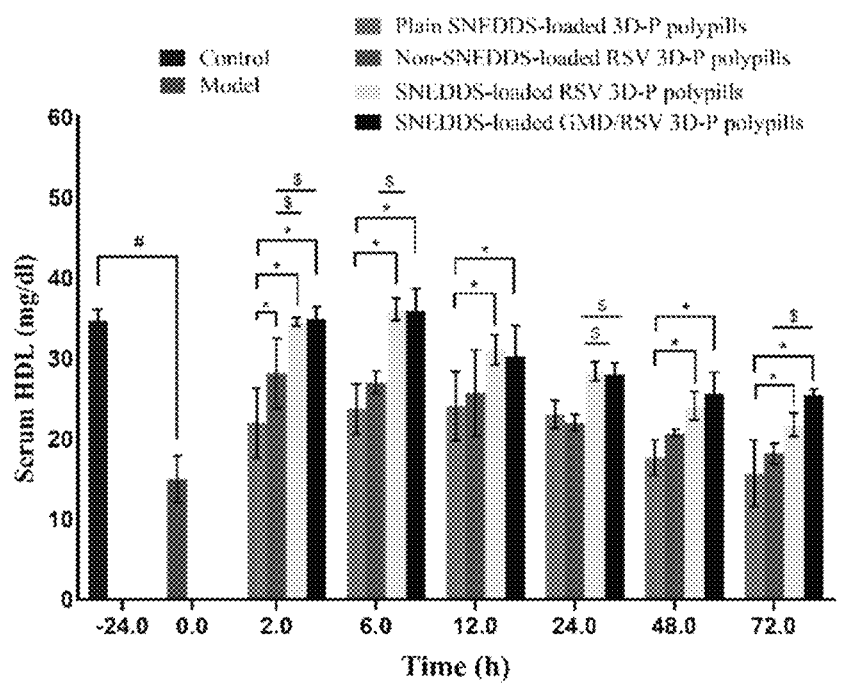
Figure 9:
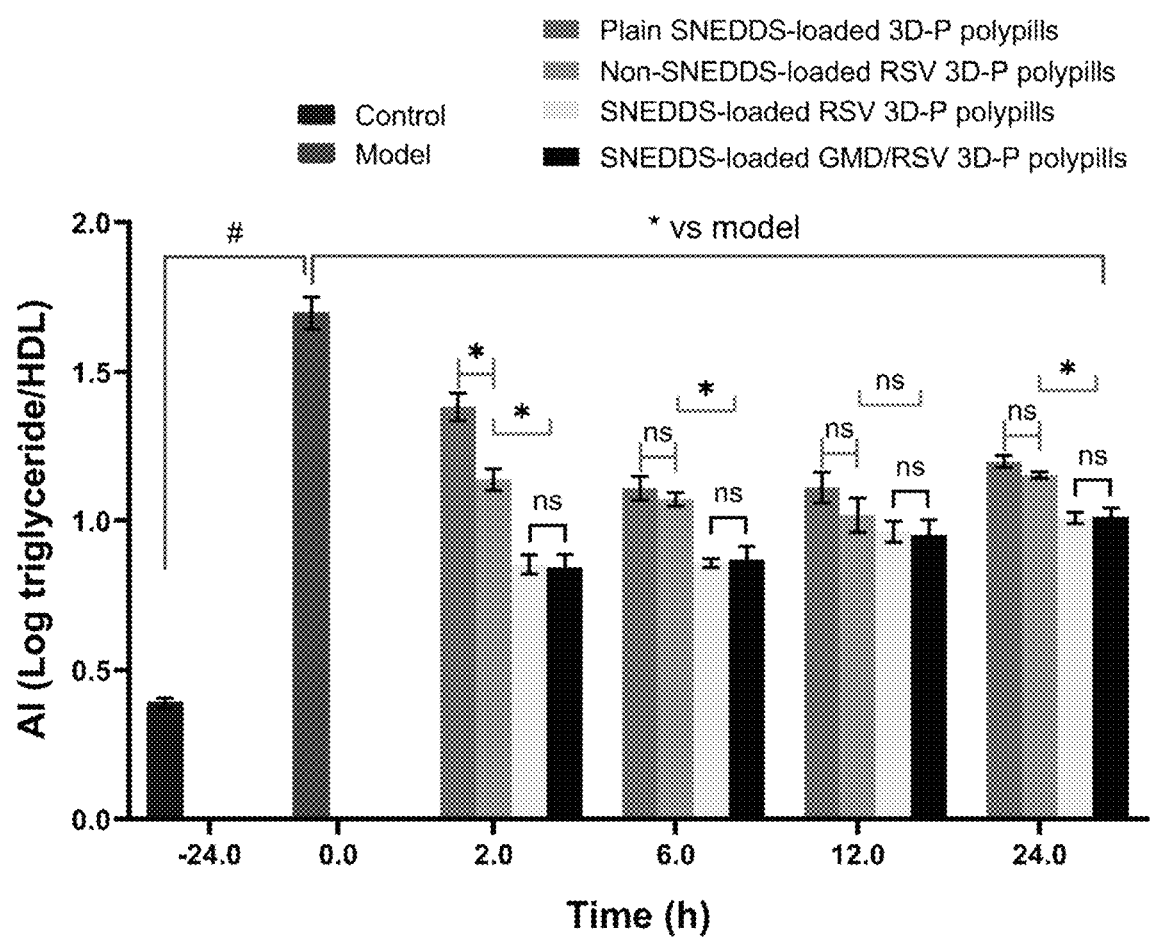
FIG. 9 shows atherosclerosis index of induced hyperlipidemic/hyperlipidemic male Wistar rats after oral administration of a single dose of the prepared 3D-printed polypills. (#) indicates significant from the control group. (*) indicates significant from the model group. Significant difference was considered at $P<0.05$. Data are presented as mean±SD, (n=3). Data are presented as mean±SEM, (n=3). Significant difference was considered at $P<0.05$.

The efficacy of the Curcuma oil SNEDDS-loaded GMD/RSV 3D-P polypills on the serum total cholesterol, triglyceride, HDL, and LDL was assessed in the induced-hyperlipidemic rat model. The observed levels of the circulating lipids were significantly increased (p<0.05) following oral administration of poloxamer 407 (FIGS. 8A-D) which confirms the induction of hyperlipidemia in the model rats compared with the normal rats. Also, the figure revealed that there is a reduction in the total cholesterol, triglyceride, and LDL with ~27%, ~50%, and ~45%, respectively after 24 h of the administration of the Curcuma oil-based SNEDDS-loaded 3D-P pills. The same behavior with a slight and insignificant difference has appeared with the non-SNEDDS-loaded RSV 3D-P pills. This finding displayed a hypolipidemic activity of Curcuma oil that is only loaded in the first formula and equivalent to the second formula that contains non-SNEDDS-loaded RSV. FIG. 8A revealed that after 24 h, the SNEDDS-loaded RSV 3D-P pills and SNEDDS-loaded GMD/RSV 3D-P polypills significantly reduced the serum total cholesterol by ~46% and ~51%, respectively which was significantly different from the corresponding plain SNEDDS and the control (P<0.05). Also, FIG. 8B displayed that the level of triglycerides in the model group was significantly higher than that in the control group (P<0.05). The marked reduction in the level of triglyceride was observed in all groups after 2 h and extended for 72 h. A significant reduction was noticed between the Curcuma oil-loaded SNEDDS and the SNEDDS-loaded RSV at all time points, but the significant difference was achieved only at 6 h between the non-SNEDDS loaded RSV pills and the SNEDDS-loaded RSV pills. An interesting finding by reducing the level of the circulating triglyceride was 60% after 24 h with the SNEDDS-loaded RSV 3D-P pills. These results implied that SNEDDS-loaded RSV 3D-P polypills have the potential in reducing the lipid contents in the serum of hyperlipidemic rats. Similarly, serum lipoproteins were also evaluated and presented in FIG. 8C-D. The LDL levels were decreased in the serum of the hyperlipidemic rats treated with SNEDDS-loaded RSV 3D-P pills and SNEDDS-loaded GMD/RSV 3D-P polypills with 58.5% and 62.5%, respectively compared with the model group after 24 h. FIG. 3C revealed that there is a significant reduction (p<0.05) in the LDL percentage over 72 h between the plain SNEDDS and non-SNEDDS-loaded RSV pills and the SNEDDS-loaded RSV pills. On the other hand, the plain SNEDDS-loaded 3D-P pills showed an elevated percentage in the circulating HDL by ~53% in comparison with its value in the model group. Also, it was noticed that there is no significant difference between these pills and the non-SNEDDS-loaded RSV 3D-P pills in the elevation percentage of HDL at the same time. But the significant difference has been verified between these two pills and the SNEDDS-loaded RSV and SNEDDS-loaded GMD/RSV 3D-P pills which produced an elevation percentage of ~89%, and ~86%, respectively. Surprisingly, the level of HDL elevation reached the normal level after 2 h with significant (p<0.05) elevation at all time points of the study between and the SNEDDS-loaded RSV and SNEDDS-loaded GMD/RSV 3D-P pills and the model group. The greater hypolipidemic activity of SNEDDS-loaded RSV 3D-P polypills can be explained by the greater solubilization of RSV, which could have increased absorption and thereby a higher plasma drug concentration (higher bioavailability) corresponding to the pharmacokinetic data. The obtained results in this study were in good agreement with a previous work that reported a reduction in the total cholesterol and LDL levels following administration of RSV solid lipid nanoparticle formulation, after 36 and 12 h, respectively, and an increase in HDL levels after 24 h [19]. FIG. 9 showed the calculated atherosclerotic index (AI) as a predictor of metabolic disorders for all groups. AI was determined according to the reported formula, log (Triglyceride/HDL) [20,21]. The figure displayed a significant decrease in the AI value between all formulations and the model group (P<0.05). Furthermore, higher significances were observed between SNEDDS-loaded RSV pills and non-SNEDDS and plain SNEDDS formulations. These outcomes suggested that RSV-loaded SNEDDS could decrease the risk of coronary disease and atherosclerosis by boosting the level of HDL and lowering both triglyceride and LDL levels.

Assessment of Hepatoprotective and Antioxidant Activity

Figure 10A:
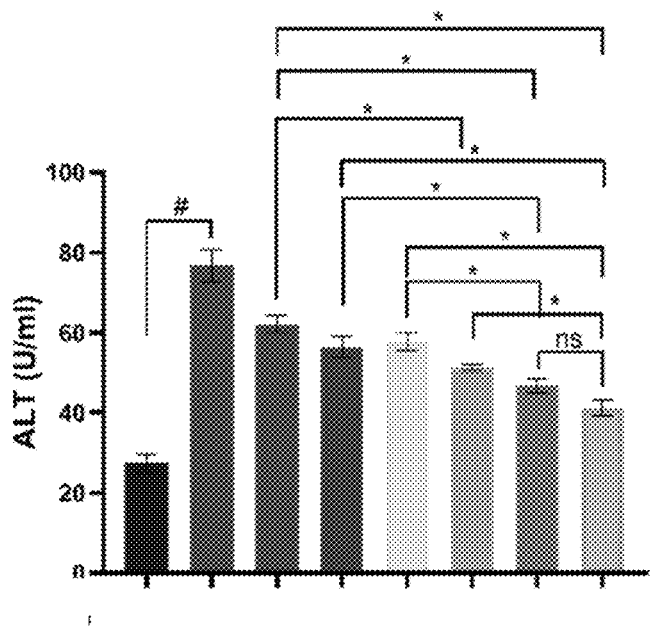
FIGS. 10A-C show serum liver enzymes (A) levels of ALT, (B) levels of AST and (C) levels of ALP of induced-hyperglycemic/hyperlipidemic male Wistar rats after oral treatment with a single dose of the prepared 3D-printed polypills. (#) indicates significant from the control group. (*) indicates significant between other groups. Significant difference was considered at $P<0.05$. Data are presented as mean±SD, (n=3).
Figure 10B:
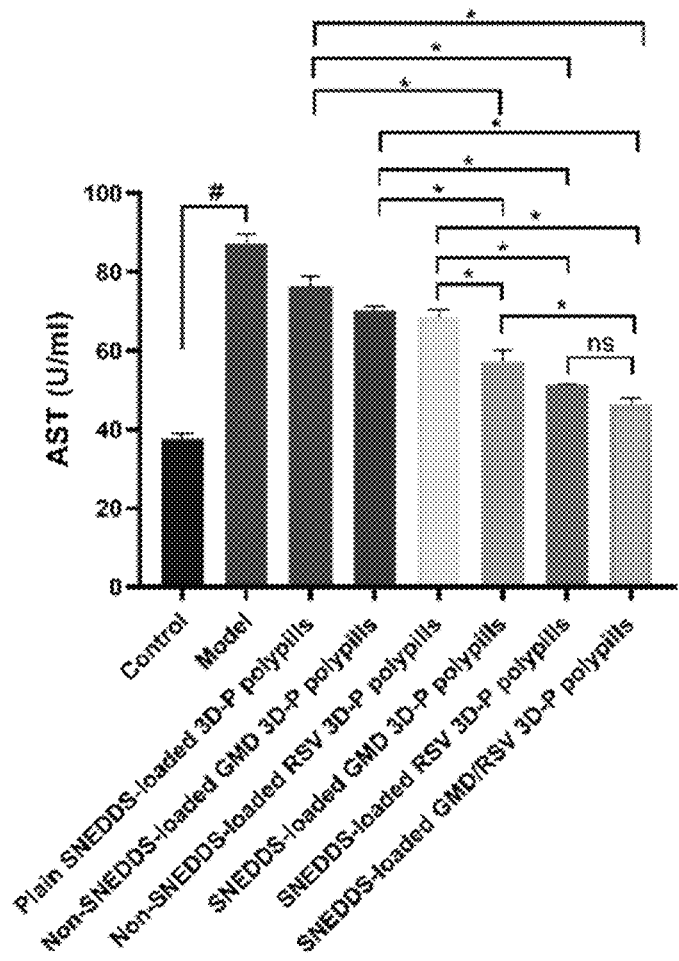
Figure 10C:
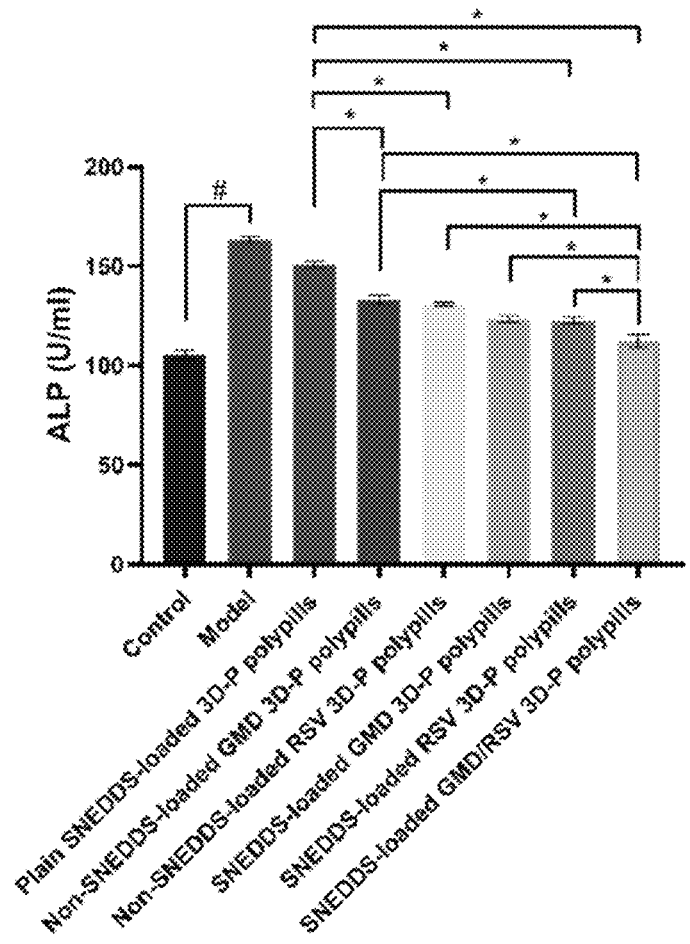

Commonly tested hepatic serum biomarkers (namely AST, ALT, and ALP) showed a dramatic increase after administration of poloxamer 407 in the induced-hyperlipidemic rats (model) that may cause liver injury. FIG. 10A-C described a significant increase (P<0.05) in the level of these liver enzymes in the model group mice in comparison with the levels of enzymes in the control mice. Markedly, the rats who were administered with either SNEDDS-loaded RSV 3D-P pills or SNEDDS-loaded GMD/RSV 3D-P pills exerted a significant improvement (P<0.05) in these parameters when compared to the groups that were given the non-SNEDDS-loaded GMD or RSV 3D-P pills, indicating the impact of the SNEDDS comprising formulations on their efficacy. Despite the significant reduction in the level of the AST and ALT after administration of SNEDDS-loaded RSV 3D-P pills or SNEDDS-loaded GMD/RSV 3D-P pills, the figure showed that there is no significant reduction between both groups except in the ALP level. Also, the figures revealed that there is a significant difference between the rats who received plain SNEDDS 3D-P pills containing only Curcuma oil and the rats who received all formulations containing GMD, RSV, or both which confirm the potential of this combination in the hepatoprotective effect. Metabolic disorders and altered liver enzymes are related to the progression of the diseases like myocardial lipidosis and profound toxicity [22].

Figure 11A:
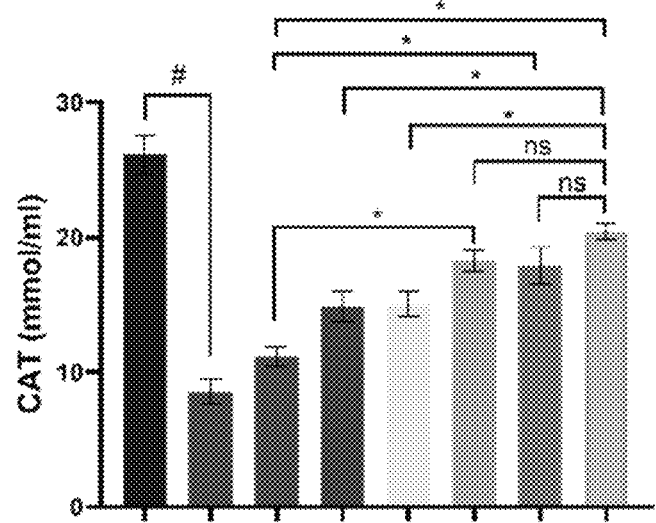
FIGS. 11A-C show antioxidant enzymes of induced-hyperglycemic/hyperlipidemic male Wistar rats after oral treatment with a single dose of the prepared 3D-printed polypills. Serum levels of (A) CAT, (B) SOD, and (C) GST. Notes: (#) indicates significant from the control group. (*) indicates significant between other groups. Significant difference was considered at $P<0.05$. Data are presented as mean±SD, (n=3).
Figure 11B:
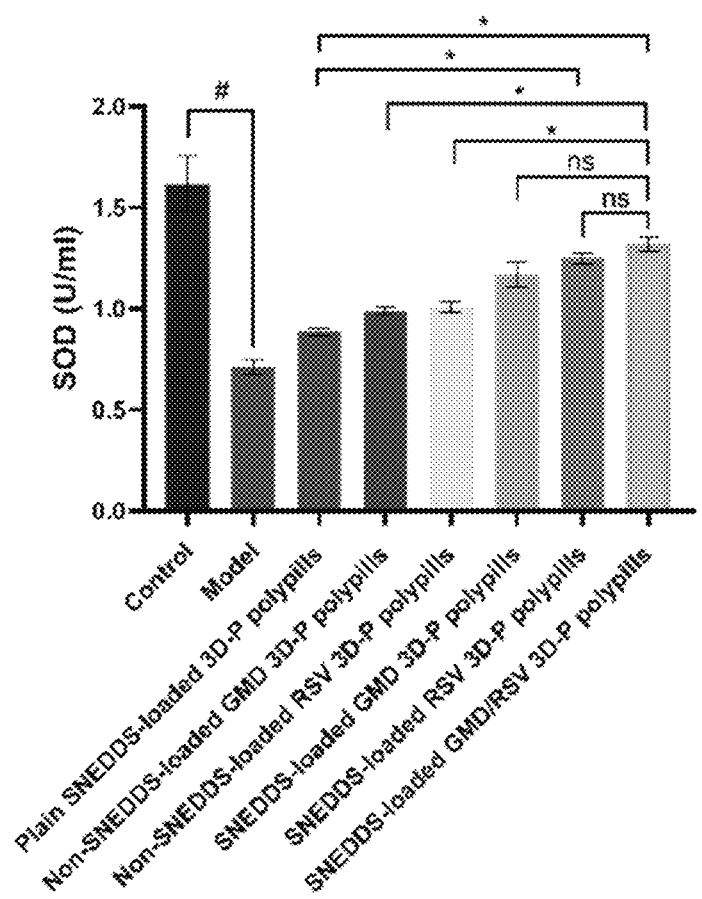
Figure 11C:
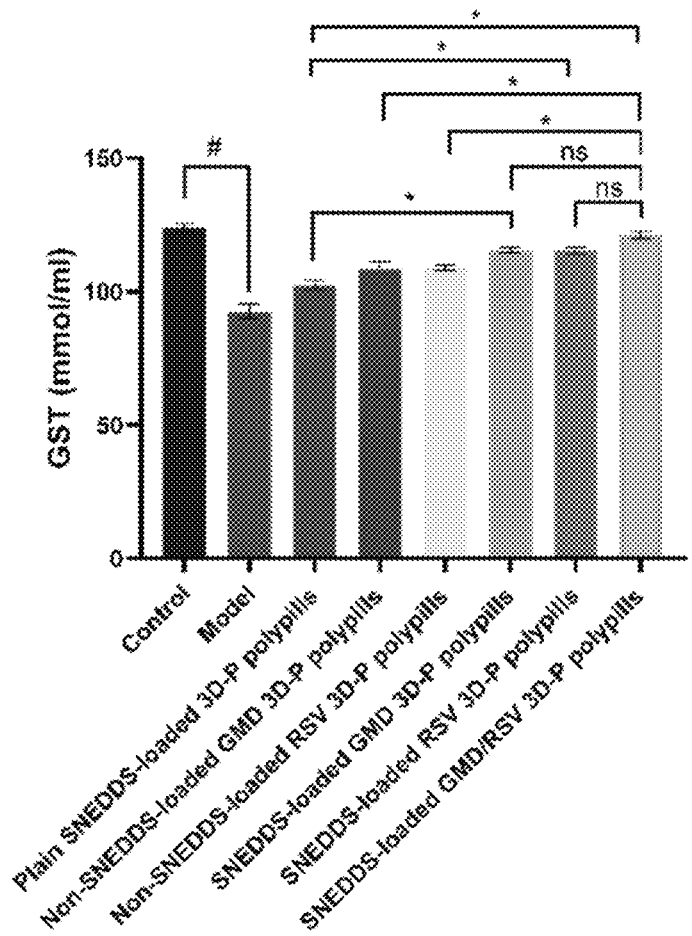

It was recently reported that RSV has an anti-inflammatory and antioxidant effect against Poloxamer 407-induced oxidative damage [23]. As shown in FIGS. 11A-C dramatic decrease with significant effect (P<0.05) in the serum CAT, SOD, and GST levels, in response to Poloxamer 407 intoxication, was observed, which indicated the presence of oxidative stress. Along with these data, the values of CAT, SOD, and GST that were increased following administration of the SNEDDS-loaded RSV 3D-P pills or SNEDDS-loaded GMD/RSV 3D-P pills were closer to the control values. Notably, rats treated with SNEDDS-loaded GMD/RSV 3D-P pills significantly upregulated the antioxidant enzymes, CAT, SOD, and GST, compared to that of the plain SNEDDS and non-SNEDDS loaded GMD or RSV (P<0.01). These results support the protective effects of SNEDDS-loaded GMD/RSV 3D-P pills against Poloxamer 407-induced oxidative damage. Furthermore, by comparing the liver functions and oxidative stress in both non-SNEDDS-treated hyperglycemic/hyperlipidemic and SNEDDS-treated hyperglycemic/hyperlipidemic groups, we found that SNEDDS-loaded GMD/RSV 3D-P polypills had a significantly more prominent reduction in serum ALT, AST, ALP levels as well as profound elevation in serum CAT, SOD, and GST levels (P<0.05).

Histopathological Examination

Figure 12A:
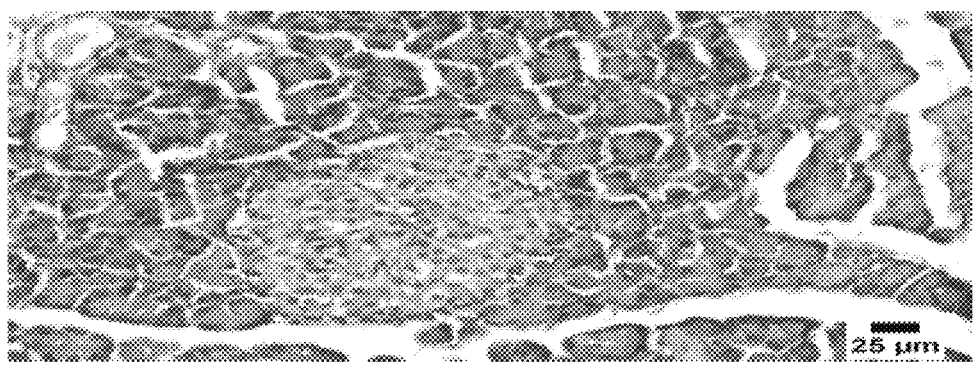
FIGS. 12A-H show histopathological images of the pancreas cells. Photomicrograph for the pancreas of the control group showing normal islets of Langerhans (A). Photomicrograph for the pancreas of the model group showing necrosis of islets of Langerhans admixed with an accumulation of eosinophilic tissue debris (indicated by an arrow) (B). Photomicrograph for the pancreas of plain SNEDDS-loaded 3D-P pills showing average-sized islets of Langerhans with few vacuolated cells (arrow) and few necrotic debris (C). Photomicrograph for the pancreas of non-SNEDDS-loaded GMD 3D-P pills showing vacuolation in the islets cells (D). Photomicrograph for the pancreas of non-SNEDDS-loaded RSV 3D-P pills showing marked vacuolation of islets cells with reduction of islets size (E). Photomicrograph for the pancreas of SNEDDS-loaded GMD 3D-P pills showing atrophy of pancreatic islet with vacuolation and mild congested blood vessel (F). Photomicrograph for the pancreas of SNEDDS-loaded RSV 3D-P pills showing mild atrophy of pancreatic islets (G). Photomicrograph for the pancreas of SNEDDS-loaded GMD/RSV 3D-P polypills showing apparently normal pancreatic islet (H).
Figure 12B:
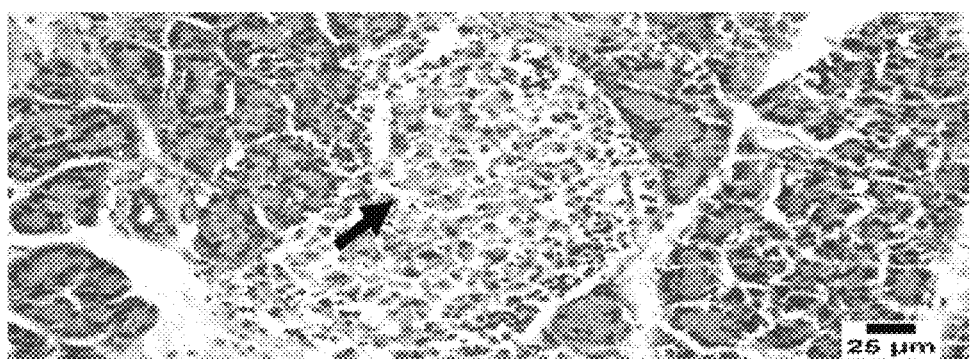
Figure 12C:
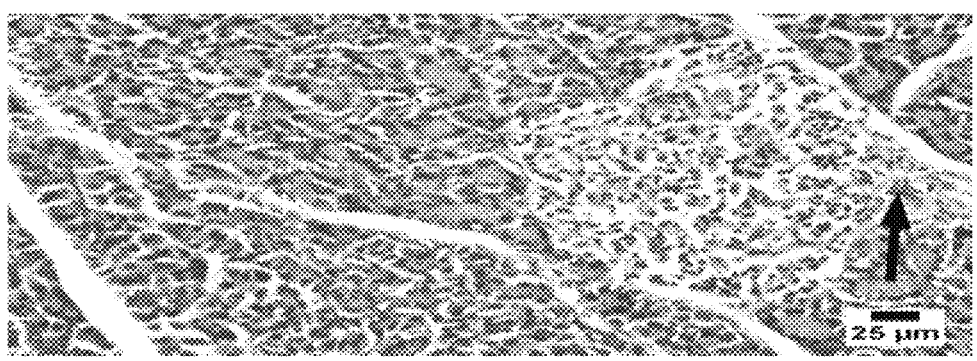
Figure 12D:
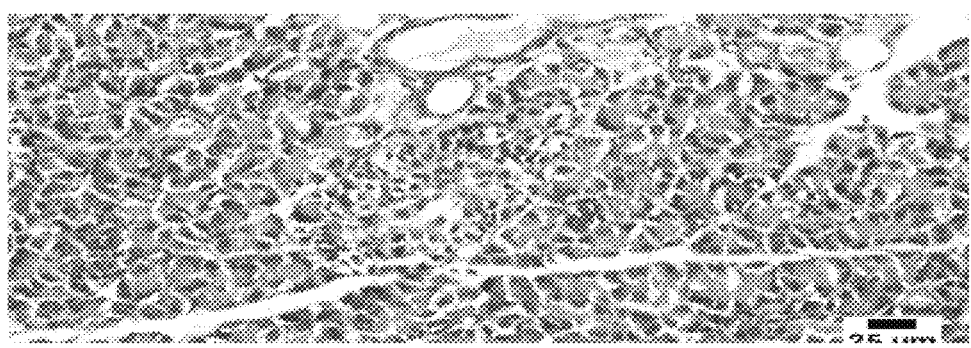
Figure 12E:
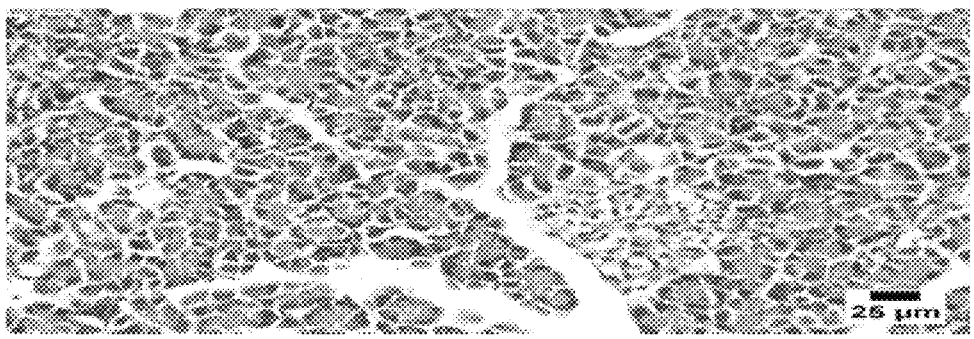
Figure 12F:
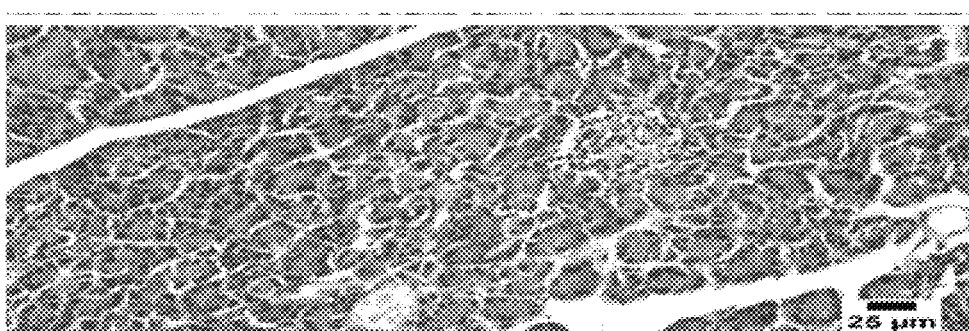
Figure 12G:
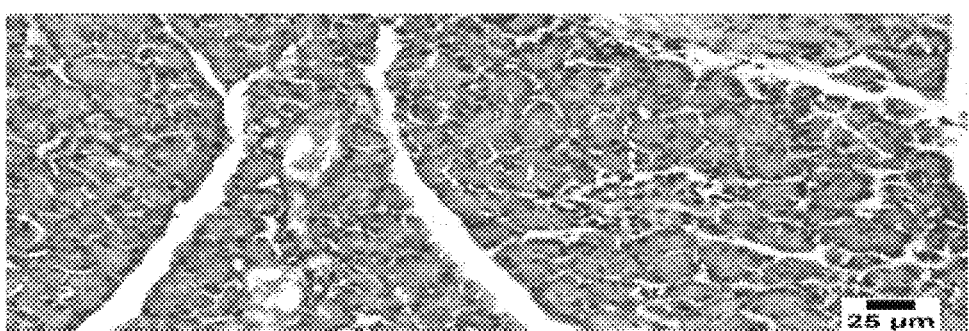
Figure 12H:
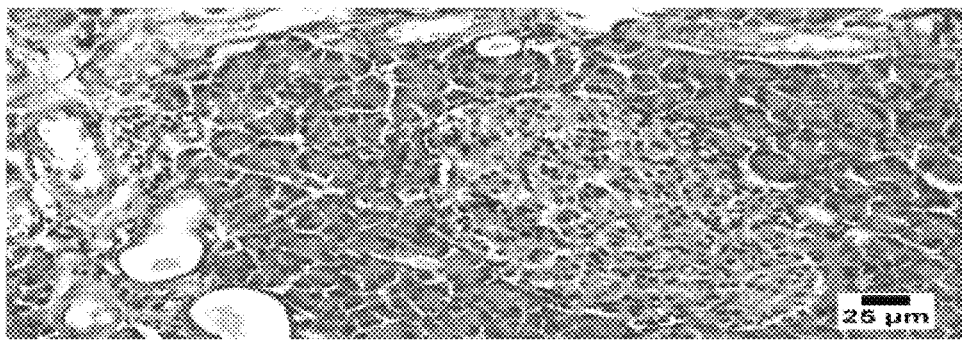

Microscopic examination of pancreas tissues of the control group (FIG. 12A) showed normal structure of both exocrine units and endocrine components. Islets of Langerhans appeared to be of normal size and contained β-cells. Pancreas tissues of the model group (FIG. 12B) showed atrophied ill-distinct islets of Langerhans that contained few vacuolated and necrotic β-cells. Necrosis of islets of Langerhans was noticed to be accompanied by eosinophilic tissue debris. Examination of group 2 (FIG. 12C) that was administered with the plain SNEDDS loaded with Curcuma oil 3D-P pills revealed mild to moderate atrophy of islets of Langerhans associated with necrobiotic changes that affected some islets which characterized by vacuolation of β-cells and few necrotic debris. Administration of non-SNEDDS-loaded GMD 3D-P pills to the rats (as shown in FIG. 12D) showed a partial improvement in the islets of Langerhans that characterized by the presence of variable-sized islets and the existence of vacuolated cells. Regarding the rats that were received non-SNEDDS-loaded RSV 3D-P pills (FIG. 12E), marked vacuolation of the islets of Langerhans cells which was frequently observed along with cystic dilated intralobular pancreatic ducts that were commonly detected in some examined sections. Administration of SNEDDS-loaded GMD 3D-P pills to animals demonstrated a partial protection of the pancreatic islets that showed variable size and vacuolation of the endocrine cells (FIG. 12F). A variable numbers of congested blood vessels were noticed in some of the affected tissue sections. Animals that received SNEDDS-loaded RSV 3D-P pills showed marked improvement in the pancreatic islets regarding the size. However vacuolated cells were still noticeable among the examined pancreatic islets (FIG. 12G). The highest protection was noticed in animals that were treated with SNEDDS-loaded GMD/RSV 3D-P polypills. The pancreatic islets of this group showed normal size islets with apparently normal pancreatic parenchyma, including exocrine acini and pancreatic duct (FIG. 12H).

Figure 13:
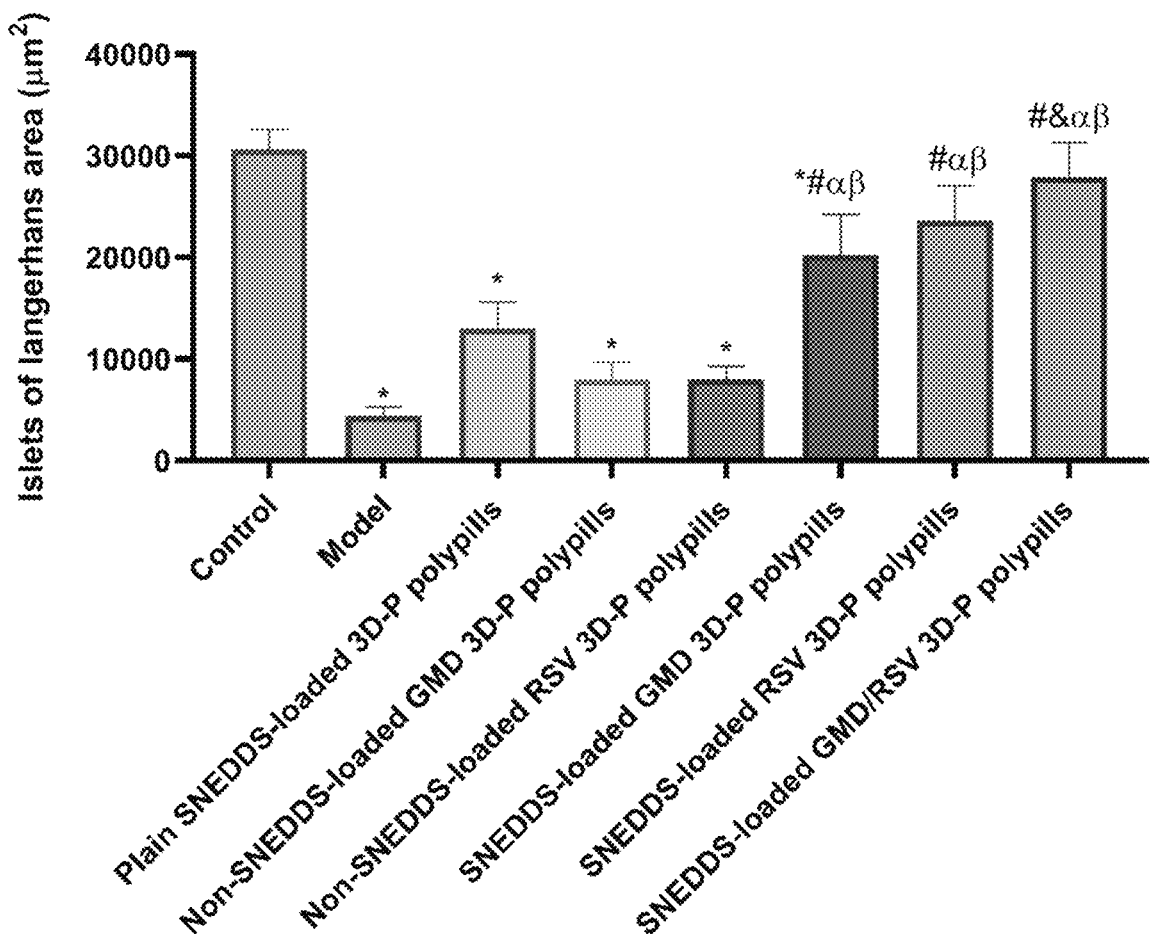
FIG. 13 shows area of islets of Langerhans in different groups. (*) indicates significant from the control group. (#) indicates significant from the model. (&) indicates significant from plain-SNEDDS-loaded 3D-P polypills. (α) indicates significant from non-SNEDDS-loaded GMD 3D-P polypills. (β) indicates significant from non-SNEDDS-loaded RSV 3D-P polypills. Data were presented as mean±SD, (n=3). Significant difference was considered at $P<0.05$.

As illustrated in FIG. 13, in all groups treated with SNEDDS-loaded formulations, the area of islets of Langerhans was decreased significantly in the model group as compared to that of the control group. The absence of significant difference was noticed between these groups and the highest pancreatic islets area average was noticed in the rats treated with SNEDDS-loaded GMD/RSV 3D-P polypills.

Figure 14A:
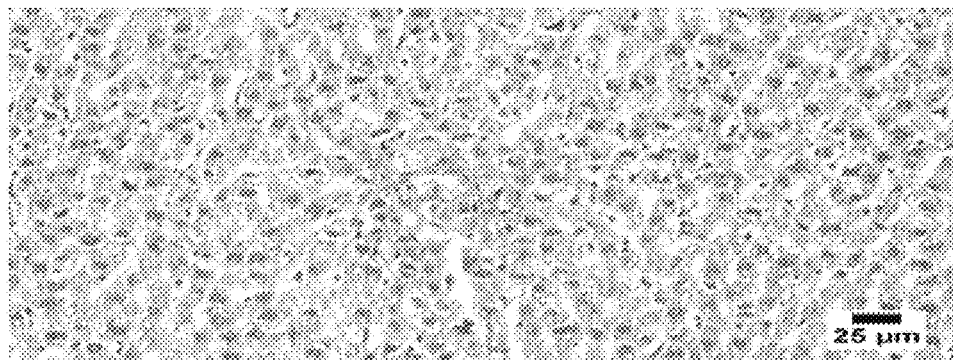
FIGS. 14A-H show histopathological images of the liver cells. Liver tissue from the control group showing normal histological structure (A). Liver tissue from the model group showing diffuse steatosis of the hepatic parenchyma (B). Liver tissue from plain-SNEDDS-loaded 3D-P polypills showing steatosis of hepatocytes (C). Liver tissue from non-SNEDDS-loaded GMD 3D-P polypills showing hemorrhages and steatosis of the hepatic parenchyma (D). Liver tissue from non-SNEDDS-loaded RSV 3D-P polypills showing widespread micro and macrovesicular steatosis in the hepatic parenchyma (E). Liver tissue from SNEDDS-loaded GMD 3D-P polypills showing apparently normal hepatocytes (F). Liver tissue from SNEDDS-loaded RSV 3D-P polypills showing mild dilation of hepatic sinusoids (G). Liver tissue from SNEDDS-loaded GMD/RSV 3D-P polypills showing apparently normal hepatic parenchyma (H).
Figure 14B:
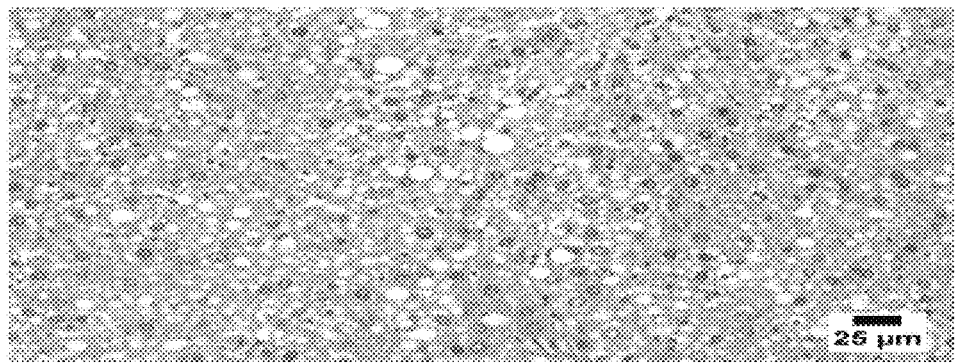
Figure 14C:
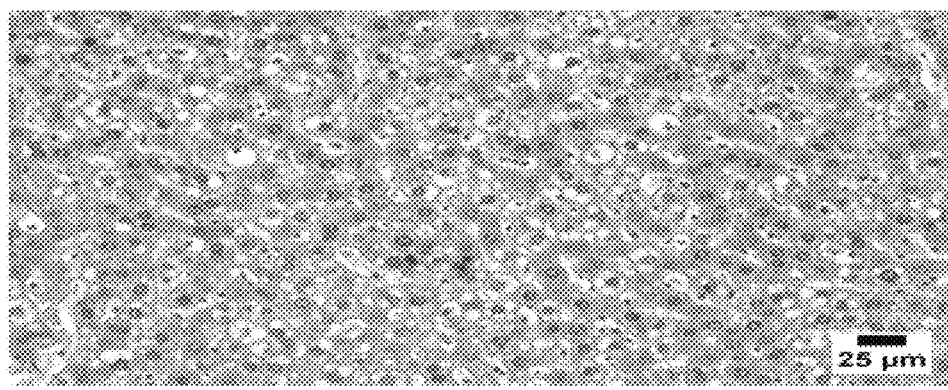
Figure 14D:
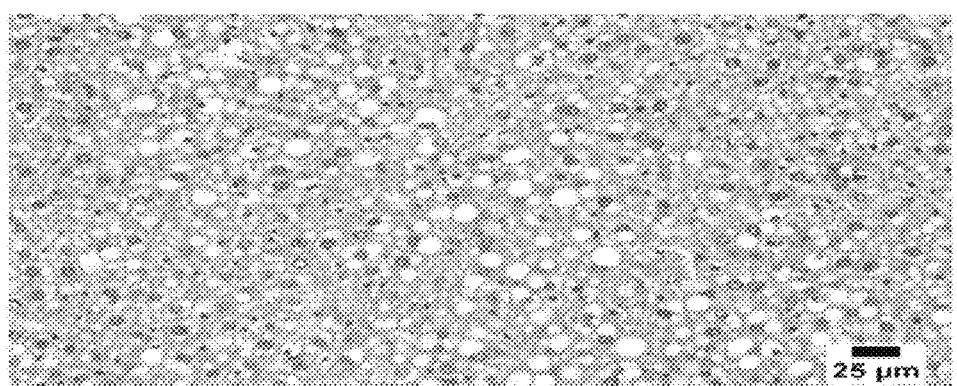
Figure 14E:
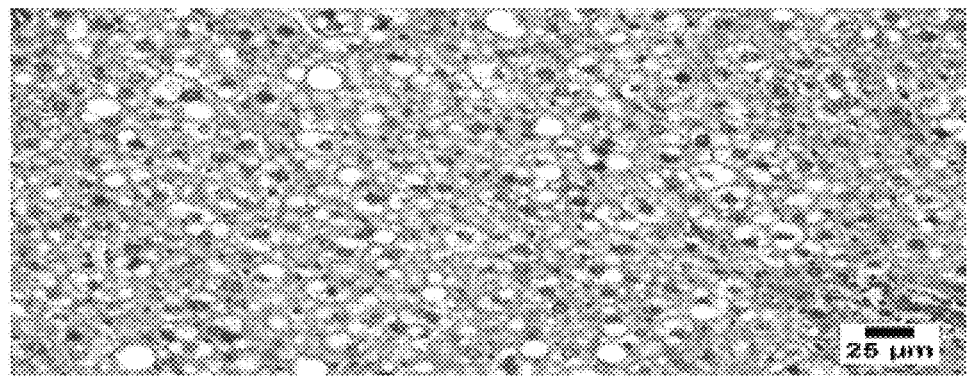
Figure 14F:
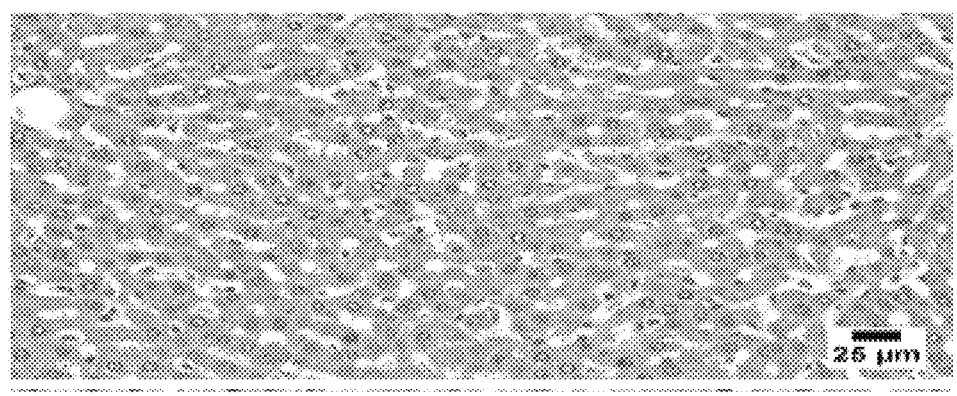
Figure 14G:
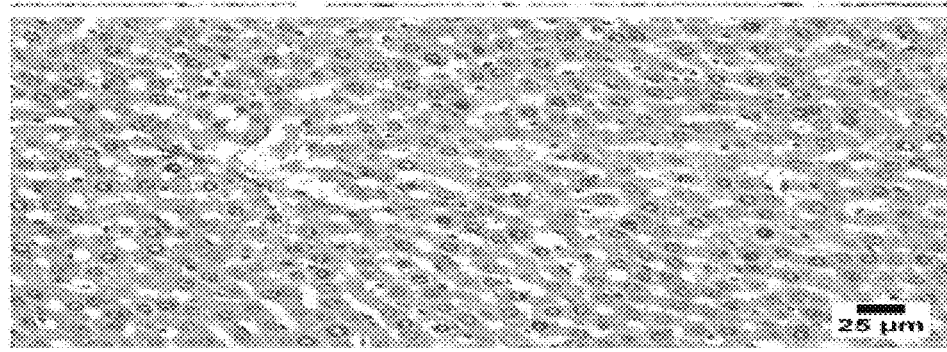
Figure 14H:
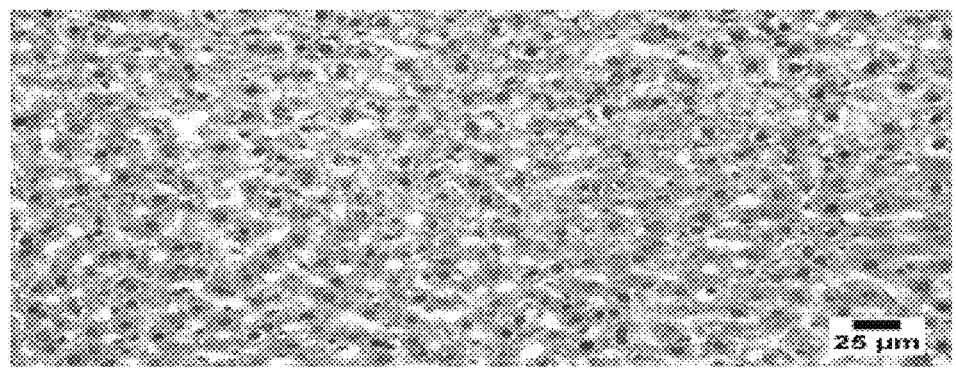
Figure 15:
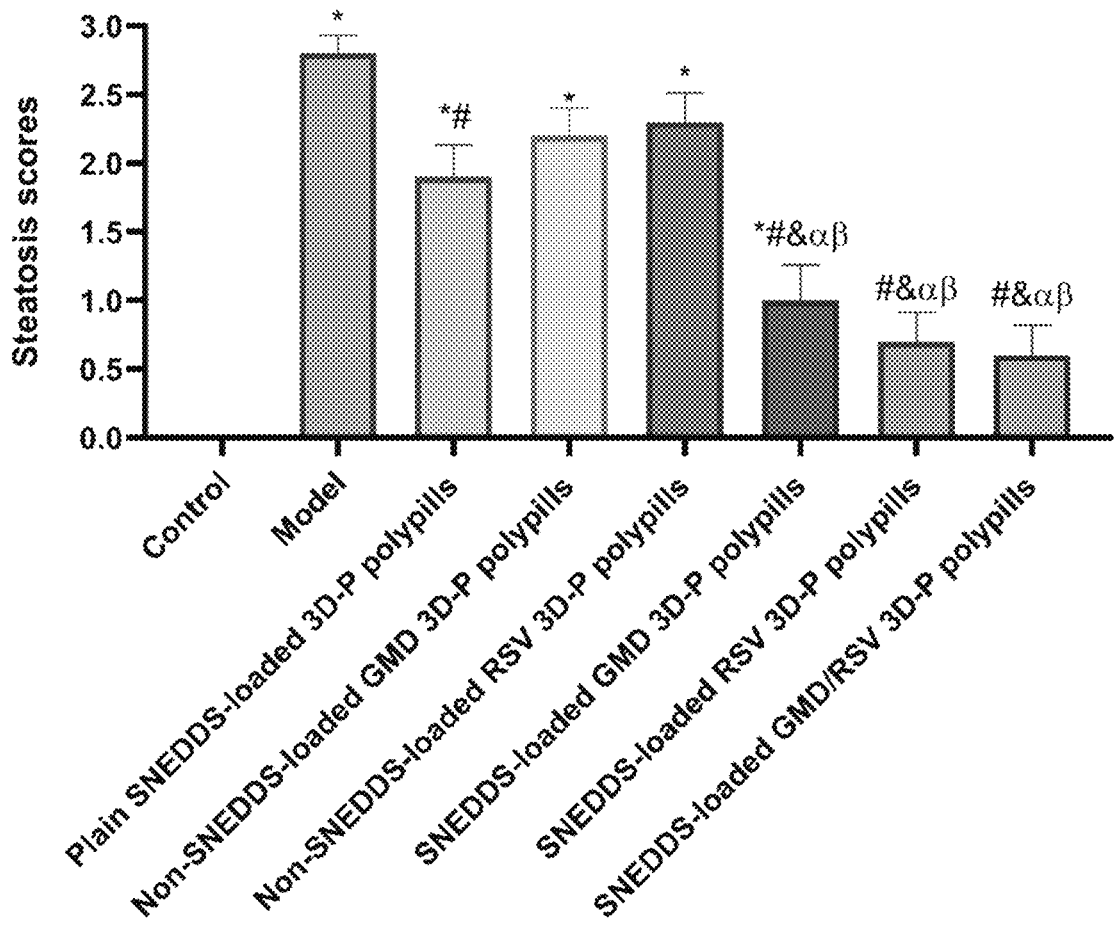
FIG. 15 shows liver steatosis lesion scores in different groups. Values were expressed as means±SE. (*) indicates significant from control. (#) indicates significant from the model. (&) indicates significant from plain-SNEDDS-loaded 3D-P polypills. (α) indicates significant from non-SNEDDS-loaded GMD 3D-P polypills. (β) indicates significant from non-SNEDDS-loaded RSV 3D-P polypills. Data were presented as mean±SD, (n=3). Significant difference was considered at $P<0.05$.

On the other hand, microscopic examination of liver tissues of the control group revealed normal hepatocytes that orderly arranged in normal lobular architecture with central veins and radiating hepatic cords. The portal triads showed normal histology containing branches of the hepatic artery, portal vein, and bile duct (FIG. 14A). Animals of the model group showed diffused steatosis of the hepatic parenchyma. The hepatocytes showed macro and microvesicular steatosis. The cytoplasm displayed a fat globule that pushed the nucleus to the periphery giving the characteristic signet ring appearance. Some examined sections showed diffuse hemorrhages and widening of hepatic sinusoids. Activation of Kupffer cells was also observed among the affected hepatic lobules associated with sporadic cell necrosis and apoptosis of hepatocytes (FIG. 14B). Administration of the plain SNEDDS loaded with Curcuma oil 3D-P pills revealed a partial protection of the hepatic parenchyma. Several examined sections showed widespread of microvascular steatosis among the hepatic lobules (FIG. 14C). Mild improvement was recorded in rats that received non-SNEDDS-loaded GMD tablets. The hepatic parenchyma showed diffuse steatosis in the hepatocytes associated with hemorrhages and expansion of hepatic sinusoids in some instances (FIG. 14D). Likewise, animals treated with non-SNEDDS-loaded RSV 3D-P pills showed marked fatty change of the affected hepatocytes associated with activation of Kupffer cells. The hepatocytes displayed large fat globules that pushed the nucleus to the periphery with a signet ring appearance (FIG. 14E). Marked protection of hepatic parenchyma was noticed in rats that were administered SNEDDS-loaded GMD 3D-P pills. Examination of hepatic tissue showed apparently normal hepatocytes. However, widening of hepatic sinusoids was commonly detected in the affected tissue (FIG. 14F). Similarly, SNEDDS-loaded RSV 3D-P pills administered to rats showed a marked enhancement in the hepatic parenchyma in several examined sections. The hepatic sinusoids were less expanded when compared to the group that received the SNEDDS-loaded GMD 3D-P pills. The hepatocytes appeared apparently normal with the absence of fat vacuoles in their cytoplasm (FIG. 14G). Finally, examination of liver sections of the animals that received SNEDDS-loaded GMD/RSV 3D-P pills showed apparently normal hepatocytes with normal hepatic sinusoids. This group illustrated the highest protection level with less detectable steatosis in the examined hepatocytes (FIG. 14H). According to the studied steatosis score, a significant decrease was detected in the rats that received the plain SNEDDS loaded with Curcuma oil 3D-P pills as well as the groups that administered SNEDDS-loaded GMD, RSV, or both when compared with the model group. Meanwhile, a significant increase was recorded in the model, and groups received non-SNEDDS-loaded GMD or RSV 3D-P pills. These findings confirm Curcuma oil as an adjunct therapy with GMD and RSV in the prophylaxis of steatosis in patients with metabolic disorders. The lowest level was detected in the rats treated with SNEDDS-loaded RSV alone or GMD/RSV polypills which showed an absence of significant difference when compared with the control group (FIG. 15).

Summary

Three-dimensional printing of polypills based on the Curcuma oil self-nanoemulsifying drug delivery system and the system loaded with glimepiride and rosuvastatin were developed. These polypills improved the pharmacokinetics of both glimepiride and rosuvastatin with $AUC_{0-t}$ values of 16,035.25 ng/ml×h and 67,811.75 ng/ml×h, respectively in comparison to the non-SNEDDS-loaded 3D-P pills. Furthermore, these polypills showed significantly superior antihyperlipidemic, hepatoprotective and antioxidant activities in mice as compared to the control and non-SNEDDS-loaded drugs. Also, SNEDDS-loaded GMD/RSV polypills could decrease the risk of coronary disease and atherosclerosis by boosting the level of HDL and lowering both triglyceride and LDL levels. After administration, no marked hepatic histopathological changes within the normal hepatic sinusoids were observed, and the polypills or tablets illustrated the highest protection level with less detectable steatosis in the examined hepatocytes. Also, microscopic examination of the pancreatic specimen showed apparently normal size pancreatic islets with normal pancreatic parenchyma including exocrine acini and pancreatic duct. All of these findings confirm Curcuma oil as an adjunct therapy component to the composition comprising GMD and RSV when given to the prophylaxis of steatosis patients with metabolic disorders and thus, this formulation is an effective personalized therapeutic for the treatment of patients with metabolic disorders.

ACKNOWLEDGEMENT

The authors extend their appreciation to the Deputyship for Research & Innovation, Ministry of Education in Saudi Arabia for funding this research work through the project number IFPRC-176-166-2020 and King Abdulaziz University, DSR, Jeddah, Saudi Arabia.

REFERENCES FOR EXAMPLES 4-6

1. USP 41-NF 36 The united States Pharmacopeia National Formulary. 2018.
2. Ahmed, O. A. A.; Ahmed, T. A.; Abdel-naim, A. B.; Khedr, A.; Banjar, Z. M.; Afouna, M. I. Enhancement of In Vitro Skin Transport and In Vivo Hypoglycemic Efficacy of Glimepiride Transdermal Patches. Trop. J. Pharm. Res. 2014, 13, 1207-1213.
3. Ahmed, T. A.; Elimam, H.; Alrifai, A. O.; Nadhrah, H. M.; Masoudi, L. Y.; Sairafi, W. O.; El-Say, K. M. Rosuvastatin lyophilized tablets loaded with flexible chitosomes for improved drug bioavailability, anti-hyperlipidemic and anti-oxidant activity. Int. J. Pharm. 2020, 588, doi:10.1016/j.ijpharm.2020.119791.
4. Mahajan, T. C.; Deshmukh, S. B.; Badgujar, V. L.; Chhajed, P. N.; Patil, J. A. RP-HPLC Method Development and Validation for estimation of Metformin, Voglibose, Glimepiride in Bulk and Combined Tablet Dosage Forms. Int. J. Chem. Pharm. Sci. 2016, 4, 697-702.
5. El-Say, K. M.; Ahmed, T. A.; Aljefri, A. H.; El-Sawy, H. S.; Fassihi, R.; Abou-Gharbia, M. Oleic Acid-Reinforced PEGylated Polymethacrylate Transdermal Film with Enhanced Antidyslipidemic Activity and Bioavailability of Atorvastatin: A Mechanistic Ex-Vivo/In-Vivo Analysis. Int. J. Pharm. 2021, 608, 121057, doi:10.1016/j.ijpharm.2021.121057.
6. E M, B.; C G, J.; A M, D. B.; B A, N.-T.; B R, B. Nonalcoholic steatohepatitis: a proposal for grading and staging the histological lesions. Am. J. Gastroenterol. 1999, 94, 2467-2474, doi:10.1111/J.1572-0241.1999.01377.X.
7. Pivari, F.; Mingione, A.; Brasacchio, C.; Soldati, L. Curcumin and type 2 diabetes mellitus: Prevention and treatment. Nutrients 2019, 11.
8. Kim, M.; Kim, Y. Hypocholesterolemic effects of curcumin via up-regulation of cholesterol 7a-hydroxylase in rats fed a high fat diet. Nutr. Res. Pract. 2010, 4, 191, doi:10.4162/nrp.2010.4.3.191.
9. Rivera-Mancía, S.; Trujillo, J.; Chaverri, J. P. Utility of curcumin for the treatment of diabetes mellitus: Evidence from preclinical and clinical studies. J. Nutr. Intermed. Metab. 2018, 14, 29-41, doi:10.1016/j.jnim.2018.05.001.
10. S F, N.; R, T.; L, R.; M, D.; E, S.-S.; H, A.; S M, N. Curcumin: a natural product for diabetes and its complications. Curr. Top. Med. Chem. 2015, 15, 2445-2455, doi:10.2174/1568026615666150619142519.
11. Sahebkar, A.; Saboni, N.; Pirro, M.; Banach, M. Curcumin: An effective adjunct in patients with statin-associated muscle symptoms? J. Cachexia. Sarcopenia Muscle 2017, 8, 19-24, doi:10.1002/jcsm.12140.
12. Marton, L. T.; Pescinini-e-Salzedas, L. M.; Camargo, M. E. C.; Barbalho, S. M.; Haber, J. F. do. S.; Sinatora, R. V.; Detregiachi, C. R. P.; Girio, R. J. S.; Buchaim, D. V.; Cincotto dos Santos Bueno, P. The Effects of Curcumin on Diabetes Mellitus: A Systematic Review. Front. Endocrinol. (Lausanne). 2021,12, doi:10.3389/fendo.2021.669448.
13. Godfrey, K. R.; Arundel, P. A.; Dong, Z.; Bryant, R. Modelling the Double Peak Phenomenon in pharmacokinetics; IFAC, 2009; Vol. 42; ISBN 9783902661494.
14. Wu, W.; Wang, Y.; Que, L. Enhanced bioavailability of silymarin by self-microemulsifying drug delivery system. Eur. J. Pharm. Biopharm. 2006, 63, 288-94, doi:10.1016/j.ejpb.2005.12.005.
15. Chang, R. K.; Shojaei, A. H. Effect of a lipoidic excipient on the absorption profile of compound UK 81252 in dogs after oral administration. J. Pharm. Pharm. Sci. 2004, 7, 8-12.
16. Al-Amodi, Y. A.; Hosny, K. M.; Alharbi, W. S.; Safo, M. K.; El-Say, K. M. Investigating the Potential of Transmucosal Delivery of Febuxostat from Oral Lyophilized Tablets Loaded with a Self-Nanoemulsifying Delivery System. Pharmaceutics 2020, 12, 1-18.
17. El-Say, K. M.; Ahmed, T. A. A.; Ahmed, O. A. A.; Elimam, H. Enhancing the Hypolipidemic Effect of Simvastatin in Poloxamer-Induced Hyperlipidemic Rats via Liquisolid Approach: Pharmacokinetic and Pharmacodynamic Evaluation. AAPS PharmSciTech 2020, 21, 223, doi:10.1208/s12249-020-01754-5.
18. El-Say, K. M.; Ahmed, T. A.; Ahmed, O. A. A.; Hosny, K. M.; Abd-Allah, F. I. Self-Nanoemulsifying Lyophilized Tablets for Flash Oral Transmucosal Delivery of Vitamin K: Development and Clinical Evaluation. J. Pharm. Sci. 2017, 106, 2447-2456, doi:10.1016/j.xphs.2017.01.001.
19. Dudhipala, N.; Veerabrahma, K. Improved anti-hyperlipidemic activity of Rosuvastatin Calcium via lipid nanoparticles: Pharmacokinetic and pharmacodynamic evaluation. Eur. J. Pharm. Biopharm. 2017, 110, 47-57, doi:10.1016/j.ejpb.2016.10.022.
20. Dobiášová, M.; Frohlich, J. The plasma parameter log (TG/HDL-C) as an atherogenic index: Correlation with lipoprotein particle size and esterification rate inapoblipoprotein-depleted plasma (FERHDL). Clin. Biochem. 2001, 34, 583-588, doi:10.1016/S0009-9120(01)00263-6.

21. Kanthe, P. S.; Patil, B. S.; Bagali, S.; Deshpande, A.; Shaikh, G. B.; Aithala, M. Atherogenic index as a predictor of cardiovascular risk among women with different grades of obesity. *Int. J. Collab. Res. Intern. Med. Public Heal.* 2012, 4, 1767-1774.

22. Hasan, K. M. M.; Tamanna, N.; Haque, M. A. Biochemical and histopathological profiling of Wistar rat treated with *Brassica napus* as a supplementary feed. *Food Sci. Hum. Wellness* 2018, 7, 77-82, doi:10.1016/j.fshw.2017.12.002.

23. Duarte, T.; Da Cruz, I. B. M.; Barbisan, F.; Capelleto, D.; Moresco, R. N.; Duarte, M. M. M. F. The effects of rosuvastatin on lipid-lowering, inflammatory, antioxidant and fibrinolytics blood biomarkers are influenced by Val16Ala superoxide dismutase manganese-dependent gene polymorphism. *Pharmacogenomics J.* 2016, 16, 501-506.

It is to be understood that this invention is not limited to any particular embodiment described herein and may vary. It is also to be understood that the terminology used herein is for the purpose of describing particular embodiments only, and is not intended to be limiting, since the scope of the present invention will be limited only by the appended claims.

Where a range of values is provided, it is understood that each intervening value between the upper and lower limit of that range (to a tenth of the unit of the lower limit) is included in the range and encompassed within the invention, unless the context or description clearly dictates otherwise. In addition, smaller ranges between any two values in the range are encompassed, unless the context or description clearly indicates otherwise.

Unless defined otherwise, all technical and scientific terms used herein have the same meaning as commonly understood by one of ordinary skill in the art to which this invention belongs. Representative illustrative methods and materials are herein described; methods and materials similar or equivalent to those described herein can also be used in the practice or testing of the present invention.

All publications and patents cited in this specification are herein incorporated by reference as if each individual publication or patent were specifically and individually indicated to be incorporated by reference, and are incorporated herein by reference to disclose and describe the methods and/or materials in connection with which the publications are cited. The citation of any publication is for its disclosure prior to the filing date and should not be construed as an admission that the present invention is not entitled to antedate such publication by virtue of prior invention. Further, the dates of publication provided may be different from the actual dates of public availability and may need to be independently confirmed.

It is noted that, as used herein and in the appended claims, the singular forms "a", "an", and "the" include plural referents unless the context clearly dictates otherwise. It is further noted that the claims may be drafted to exclude any optional element. As such, this statement is intended to serve as support for the recitation in the claims of such exclusive terminology as "solely," "only" and the like in connection with the recitation of claim elements, or use of a "negative" limitations, such as "wherein [a particular feature or element] is absent", or "except for [a particular feature or element]", or "wherein [a particular feature or element] is not present (included, etc.) . . . ".

As will be apparent to those of skill in the art upon reading this disclosure, each of the individual embodiments described and illustrated herein has discrete components and features which may be readily separated from or combined with the features of any of the other several embodiments without departing from the scope or spirit of the present invention. Any recited method can be carried out in the order of events recited or in any other order which is logically possible.

What is claimed is:

1. A method of treating a metabolic disorder or disease in a subject in need thereof, comprising
administering to the subject a therapeutically effective amount of a 3D-printed tablet, wherein the 3D-printed tablet comprises glimepiride (GLMP) and rosuvastatin (RSV) or pharmaceutically acceptable salts thereof, and 10-20 wt. % of curcuma oil in a self-nanoemulsifying drug delivery system (SNEDDS),
wherein the 3D-printed tablet is a multi-compartmentalized tablet having at least one layer of GLMP and at least one layer of RSV in separate compartments, wherein each compartment is configured to release GLMP or RSV at a different rate,
wherein the GLMP and rosuvastatin RSV are at a weight ratio of about 3:1 to 1:3, and
wherein the metabolic disorder or disease is selected from the group consisting of diabetes, hyperlipidemia, and liver disease.

2. The method of claim 1, wherein the metabolic disorder or disease is diabetes.

3. The method of claim 1, wherein the metabolic disorder or disease is hyperlipidemia.

4. The method of claim 1, wherein the metabolic disorder or disease is fatty liver disease.

5. The method of claim 1, wherein the 3D-printed tablet is orally, rectally, or vaginally administered.

6. The method of claim 1, wherein the subject is a human.

7. The method of claim 1, wherein the subject is a non-human animal.

8. The method of claim 1, wherein multiple doses of the 3D-printed tablet are administered to the subject.

9. The method of claim 8, wherein the 3D-printed tablet is administered daily.

10. The method of claim 8, wherein the 3D-printed tablet is administered weekly.

11. The method of claim 8, wherein the 3D-printed tablet is administered monthly.

12. The method of claim 8, wherein the 3D-printed tablet is administered three times a day.

13. The method of claim 8, wherein the 3D-printed tablet is administered twice a day.

* * * * *